US010660352B2

(12) United States Patent
Massey et al.

(10) Patent No.: US 10,660,352 B2
(45) Date of Patent: May 26, 2020

(54) ANTIMICROBIAL APPLICATION SYSTEM WITH RECYCLE AND CAPTURE

(71) Applicant: SAFE FOODS CORPORATION, North Little Rock, AR (US)

(72) Inventors: Justin Massey, North Little Rock, AR (US); Tim Yeaman, North Little Rock, AR (US); Gary Nolen, Fayetteville, AR (US); Kelly Beers, Fayetteville, AR (US); Joe Rheingans, Rogers, AR (US)

(73) Assignee: SAFE FOODS CORPORATION, North Little Rock, AR (US)

( * ) Notice: Subject to any disclaimer, the term of this patent is extended or adjusted under 35 U.S.C. 154(b) by 1 day.

(21) Appl. No.: 16/128,724

(22) Filed: Sep. 12, 2018

(65) Prior Publication Data
US 2019/0030464 A1 Jan. 31, 2019

Related U.S. Application Data

(60) Continuation of application No. 15/069,255, filed on Mar. 14, 2016, now abandoned, which is a division of
(Continued)

(51) Int. Cl.
*A23L 3/3589* (2006.01)
*B01D 24/40* (2006.01)
(Continued)

(52) U.S. Cl.
CPC .............. *A23L 3/3589* (2013.01); *A23B 4/20* (2013.01); *A23B 4/24* (2013.01); *A23B 4/26* (2013.01);
(Continued)

(58) Field of Classification Search
CPC ........ B01D 33/11; B01D 33/41; B01D 33/50; B01D 2201/084; B01D 2201/307;
(Continued)

(56) References Cited

U.S. PATENT DOCUMENTS 176,896 A    5/1876  Smith
3,260,369 A  7/1966  Gruenewaelder
(Continued)

FOREIGN PATENT DOCUMENTS

EA    200501190 A1    6/2006
GB       1342082 A   12/1973
(Continued)

OTHER PUBLICATIONS

Examination Report No. 1 received in Australian Application No. 2018236773, dated Apr. 10, 2019.
(Continued)

*Primary Examiner* — Benjamin M Kurtz
(74) *Attorney, Agent, or Firm* — Haynes and Boone, LLP

(57) ABSTRACT

A capture unit for use with an antimicrobial application unit may include an upstream filter and a downstream filter. The upstream filter may be positioned to receive effluent from the application unit and to filter solid components from the effluent. The resultant upstream effluent filtrate may then be passed downstream to the downstream filter. The downstream filter may be used to filter an antimicrobial component from the upstream effluent filtrate and the resultant downstream effluent filtrate may be suitable for disposal as wastewater discharge. The antimicrobial is preferably a quaternary ammonium compound, is more preferably an alkylpyridinium chloride, and is most preferably cetylpyridinium chloride.

20 Claims, 9 Drawing Sheets

Related U.S. Application Data application No. 14/510,385, filed on Oct. 9, 2014, now Pat. No. 9,352,983, which is a continuation-in-part of application No. 10/535,030, filed as application No. PCT/US03/35933 on Nov. 12, 2003, now Pat. No. 9,072,315.

(60) Provisional application No. 60/425,679, filed on Nov. 12, 2002.

(51) Int. Cl.

| | | |
|---|---|---|
| B01D 24/24 | (2006.01) | |
| B01D 24/00 | (2006.01) | |
| C02F 1/50 | (2006.01) | |
| C02F 1/28 | (2006.01) | |
| B01D 33/50 | (2006.01) | |
| B01D 33/11 | (2006.01) | |
| A61L 2/24 | (2006.01) | |
| A23B 4/24 | (2006.01) | |
| A23L 3/3454 | (2006.01) | |
| A61L 2/18 | (2006.01) | |
| A23L 3/3526 | (2006.01) | |
| A23L 3/3463 | (2006.01) | |
| A23B 4/26 | (2006.01) | |
| A23B 4/20 | (2006.01) | |
| B01D 33/41 | (2006.01) | |
| C02F 103/32 | (2006.01) | |

(52) U.S. Cl.
CPC ........... *A23L 3/3454* (2013.01); *A23L 3/3463* (2013.01); *A23L 3/3526* (2013.01); *A61L 2/18* (2013.01); *A61L 2/24* (2013.01); *B01D 24/007* (2013.01); *B01D 24/24* (2013.01); *B01D 24/40* (2013.01); *B01D 33/11* (2013.01); *B01D 33/50* (2013.01); *C02F 1/283* (2013.01); *C02F 1/50* (2013.01); *B01D 33/41* (2013.01); *B01D 2201/084* (2013.01); *C02F 2103/32* (2013.01); *C02F 2209/005* (2013.01); *C02F 2303/18* (2013.01); *C02F 2303/185* (2013.01); *C02F 2303/24* (2013.01)

(58) Field of Classification Search
CPC ...... B01D 24/007; B01D 24/24; B01D 24/40; B01D 35/308
USPC ................. 210/287–289, 394, 403, 263, 282
See application file for complete search history.

(56) References Cited

U.S. PATENT DOCUMENTS

| | | |
|---|---|---|
| 3,384,240 A | 5/1968 | Berardi |
| 3,809,247 A | 5/1974 | Brett |
| 4,199,449 A | 4/1980 | Slejko |
| 4,368,125 A | 1/1983 | Murray |
| 4,379,750 A | 4/1983 | Tiggelbeck |
| 4,586,287 A | 5/1986 | Bleasdale et al. |
| RE32,695 E | 6/1988 | Nahra et al. |
| 4,753,726 A | 6/1988 | Suchanek |
| 4,906,381 A | 3/1990 | Barbaro |
| 4,965,911 A | 10/1990 | Davey |
| 4,996,070 A | 2/1991 | Nafisi-Movaghar |
| 5,133,860 A | 7/1992 | Tai |
| 5,399,541 A | 3/1995 | Ishii et al. |
| 5,421,883 A | 6/1995 | Bowden |
| 5,968,338 A | 10/1999 | Hulme et al. |
| 5,980,375 A | 11/1999 | Anderson et al. |
| 6,126,810 A | 10/2000 | Fricker et al. |
| 7,651,614 B2 | 1/2010 | Kelsey et al. |
| 8,012,002 B2 | 9/2011 | Brown |
| 9,185,929 B2 | 11/2015 | Nolen et al. |
| 9,345,262 B2 | 5/2016 | Nolen et al. |
| 9,352,983 B2 | 5/2016 | Massey et al. |
| 2002/0064585 A1 | 5/2002 | Christianson et al. |
| 2002/0074292 A1 | 6/2002 | Schlegel et al. |
| 2003/0047087 A1 | 3/2003 | Phebus et al. |
| 2003/0136862 A1 | 7/2003 | Filicicchia et al. |
| 2004/0115322 A1 | 6/2004 | Osborn |
| 2004/0195167 A1 | 10/2004 | Kamo et al. |
| 2007/0025897 A1 | 2/2007 | Rheingans et al. |
| 2008/0241269 A1 | 10/2008 | Velasquez |
| 2009/0107919 A1 | 4/2009 | Burba et al. |
| 2010/0123028 A1 | 5/2010 | Rayner |
| 2011/0297609 A1 | 12/2011 | Hu |
| 2011/0309036 A1 | 12/2011 | Hussam et al. |
| 2012/0255896 A1 | 10/2012 | Courtemanche et al. |
| 2016/0262439 A1 | 9/2016 | Nolen et al. |

FOREIGN PATENT DOCUMENTS

| | | |
|---|---|---|
| GB | 2408001 A | 5/2005 |
| JP | 1979-104500 A | 8/1979 |
| JP | 1998-165723 A | 6/1998 |
| JP | 2006-509499 A | 3/2006 |
| JP | 2007-216195 A | 8/2007 |
| RU | 2152273 C1 | 7/2000 |
| RU | 65783 U1 | 8/2007 |
| RU | 93297 U1 | 4/2010 |
| RU | 118873 U1 | 8/2012 |
| WO | WO 2004043162 A2 | 5/2004 |
| WO | WO 2007147228 A1 | 12/2007 |
| WO | WO 2011029205 A1 | 3/2011 |
| WO | WO 2016057295 A1 | 4/2016 |

OTHER PUBLICATIONS

International Preliminary Examination Report, issued in PCT/US2003/035933, dated Sep. 25, 2005.
International Search Report, issued in PCT/US2015/053398, dated Feb. 2, 2016.
Technical Examination of the Substance of the Application issued by the Ministry of Commerce and Industries of the Republic of Panama in Application No. 91583-01 dated Sep. 11, 2017. (1 page).
Examination Report for New Zealand Patent Application No. 730587 prepared by the New Zealand Intellectual Property Office dated Sep. 25, 2017. (8 pages).
Examination Report for Australian Patent Application No. 2015328488 prepared by the Australian Intellectual Property Office dated Mar. 8, 2018. (4 pages).
Examination Report for European Patent Application No. 15848776.9 prepared by the European Patent Office dated Mar. 26, 2018. (10 pages).
Examination Report for Singaporean Patent Application No. 11201702575W prepared by the Intellectual Property Office of Singapore dated Apr. 2, 2018. (6 pages).
Examination Report for Russian Patent Application No. 2017111809 prepared by the Federal Service for Intellectual Property dated Apr. 18, 2018 and English translation thereof. (12 pages).
First Examination Report for New Zealand Patent Application No. 750496, prepared by New Zealand Intellectual Property Office, dated Jun. 19, 2019, (2 pgs.).
First Substantive Examination Report for Malaysian Patent Application PI 2017701213 by Intellectual Property Corporation of Malaysia, dated Jun. 26, 2019, (3 pgs.).
English Translation of First Office Action for Japanese Patent Application No. 2017-516752 by the Japan Patent Office, dated Jul. 2, 2019, (4 pgs.).
Examiner Report for Canadian Patent Application No. 2,963,638, prepared by the Canadian Intellectual Property Office (CIPO), dated Jul. 26, 2018, (4 pgs).
Expert Examiner Report on Application for Invention Patent for Chilean Patent Application No. 201700831, prepared by the Chilean Patent and Trademark Office, English translation, dated Jul. 23, 2018 (14 pgs).

(56) References Cited

OTHER PUBLICATIONS

Examiner's Opinion for Colombian Patent Application No. NC2017/0003899, prepared by the Colombian Patent and Trademark Office, English translation, dated Sep. 25, 2018, (4 pgs).
European Search Report for European Patent Application No. EP15848776.9, prepared by the European Patent Office, dated Jul. 4, 2018 (8 pgs).
First Examination Report for New Zealand Patent Application No. 740977, prepared by New Zealand Intellectual Property Office, dated Aug. 10, 2018, (3 pgs.).
Decision to Grant for Russia Patent Application No. 2017111809/05(020846), prepared by Federal Service for Intellectual Property (Rospatent) and English translation, dated Aug. 29, 2018, (15 pgs.).
Examination Report for Panamanian Patent Application No. 91583-01 prepared by the General Directorate of Industrial Property Registration (DIGERPI) dated Sep. 11, 2017. (2 pages).

ANTIMICROBIAL APPLICATION SYSTEM WITH RECYCLE AND CAPTURE

CROSS-REFERENCE TO RELATED APPLICATIONS

This application is a continuation of U.S. patent application Ser. No. 15/069,255, filed Mar. 14, 2016, which is a divisional of U.S. patent application Ser. No. 14/510,385, filed Oct. 9, 2014, which issued as U.S. Pat. No. 9,352,983 on May 11, 2016, which is a continuation-in-part of U.S. patent application Ser. No. 10/535,030, filed Oct. 10, 2008, which issued as U.S. Pat. No. 9,072,315 on Jul. 7, 2015, which is the National Stage of International Patent Application No. PCT/US2003/035933, filed Nov. 12, 2003, and which claims the benefit of U.S. Provisional Application No. 60/425,679, filed Nov. 12, 2002.

BACKGROUND

This invention relates to an antimicrobial application system, and more particularly to an antimicrobial application system with recycle features for use in connection with food products and surfaces and other items associated with food processing.

Antimicrobial application systems, including spray cabinets are known in the art. U.S. Pat. No. 6,742,720, issued Jun. 1, 2004, titled Spray application System, discusses a number of such systems and highlights a number of the advantages and disadvantages of these systems. The disclosure of U.S. Pat. No. 6,742,720 is incorporated herein by reference. The spray application systems disclosed in that patent offer a number of advantages over earlier systems, as discussed in more detail in that patent. Still, the present inventors have further refined and built upon those systems to offer alternate embodiments offering additional flexibility. For example, it may be desirable to recycle the antimicrobial that is applied to the work pieces. Adding equipment and steps to allow for recycling adds to the cost and complexity of a system, so it will not always be preferred. Still, using recycling reduces consumption of the antimicrobial and water and reduces the amount of waste material in need of disposal. This may be desirable for any number of reasons such as environmental concerns, raw material costs, raw material storage limitations, disposal costs, and regulatory issues involving disposal of wastewater and some antimicrobials. Accordingly, under many circumstances, it will be desirable to recycle the antimicrobial for multiple applications to work pieces to be treated.

Recycling of liquids applied to some types of work pieces in a process line is generally known in the art. Still, recycling liquids in connection with food processing and items associated with food processing presents a number of special issues and concerns, particularly concerning adulteration, contamination, and cross-contamination. These concerns typically argue against recycling or lead to the use of slow, cumbersome, undesirable extra steps and extra equipment that add to the cost and complexity of a system. One such complex system is disclosed in U.S. Pat. No. 6,348,227, issued to Caracciolo, Jr. in 2002, the disclosure of which is incorporated herein by reference.

SUMMARY

In one aspect, a capture unit for use with an antimicrobial application unit includes an upstream filter and a downstream filter. The upstream filter may be configured to be coupled to an upstream capture line for carrying effluent from the antimicrobial application unit to the upstream filter. The downstream filter may be configured to be coupled to a downstream capture line for carrying the upstream effluent filtrate to the downstream filter. The upstream filter may be further configured to filter a solid component of the effluent and the downstream filter may be further configured to filter an antimicrobial component of the effluent.

In various embodiments, the upstream filter may comprise a screen filter that includes a body having a first end, a second end, and an annular wall extending therebetween. The annular wall may define a bore that extends through the body for receiving the effluent from the upstream capture line. The annular wall may comprise a filter portion having a plurality of perforations extending through the annular wall to filter a solid component of the effluent when the effluent is received within the bore from the upstream capture line. The body may be rotatable about a rotation axis extending through the bore. The annular wall may further comprise a band portion having a continuous surface along the inwardly facing surface and extending about the bore. The band portion may be configured to receive the effluent from the upstream capture line onto the continuous surface before the effluent passes to the filter portion. The screen filter may further comprise a thread protruding from the inwardly facing surface of the annual wall into the bore and that helically extends along the inwardly facing surface between the first end and the second end of the body. The annular wall may further comprise a delivery region configured to receive the effluent from the upstream capture line. The delivery region includes a continuous surface forming a band along the inwardly facing surface and extending about the bore. The thread may extend along the filter portion and the continuous surface. The screen filter may further comprise a cleaner configured to remove filtered solid components from the annular wall. The cleaner may comprise a spray bar including one or more fluid ports positioned to direct fluid toward the annular wall. The fluid ports may be positioned outside the bore.

In various embodiments, the downstream filter comprises at least two filter units, each comprising a container configured to retain a filter material comprising activated carbon. The filter units may be aligned in series and configured to filter the antimicrobial component from the upstream effluent filtrate. In one application, the antimicrobial component comprises a quaternary ammonium compound. At least one of the filter units may include a header comprising a body having an upstream inlet and a plurality of downstream fluid ports positioned along a plurality of arms. In one embodiment, the body may comprise at least four arms arranged in an "X" configuration. In one embodiment, the body includes at least two arms, each defining at least twenty fluid ports. The fluid ports may be positioned on at least two sides of each arm. The fluid ports may define cross-sections between 0.125 to 0.250 inches. At least one of the containers may comprise an inner surface formed of a plastic.

In another aspect, an antimicrobial carbon filtration system comprises a header. The header may include a body having an upstream inlet and a plurality of downstream fluid ports positioned along a plurality of arms. The header may be configured to be positioned at an upstream portion of a filter container to distribute a fluid containing an antimicrobial component to be separated onto a filter material.

In one embodiment, the body may include at least two arms, each defining at least twenty fluid ports. The fluid ports may be positioned on at least two sides of each arm. The fluid ports may further define cross-sections between 0.125 to 0.250 inches. In one embodiment, the header may comprise at least four arms arranged in an "X" configuration. In a further embodiment, the body may include four arms arranged in an "X" configuration and the fluid ports may define cross-sections between 0.125 to 0.250 inches.

In yet another aspect, an antimicrobial carbon filtration system comprises a filter unit container. The filter unit container may have an outer wall and a plastic inner wall. The plastic inner wall may define a bore configured to retain a filter material comprising activated carbon.

In various embodiments, the outer wall comprises a metal drum. The filter unit container may further comprise a removable liner and the removable liner may comprise the inner wall. The outer wall may be formed of plastic and the filter unit container may comprise a plastic drum.

BRIEF DESCRIPTION OF THE DRAWINGS

The above brief description, as well as further objects, features and advantages of the present embodiments will be more fully appreciated by reference to the following detailed description of the presently preferred but nonetheless illustrative embodiments in accordance with the present embodiments when taken in conjunction with the accompanying drawings, wherein.

DESCRIPTION

Figure 1:
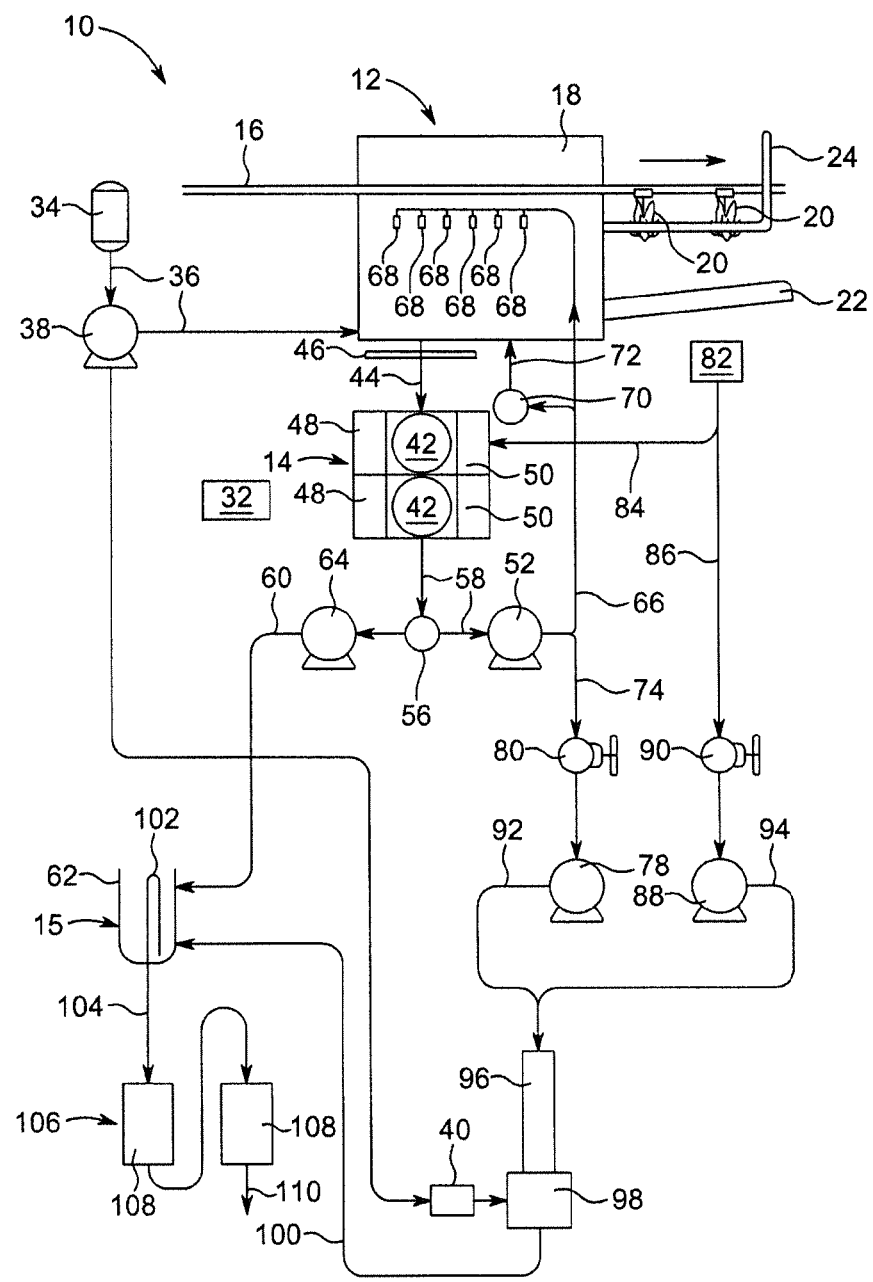
FIG. 1 is a schematic view of an antimicrobial application system according to various embodiments described herein.

Various embodiments are described and illustrated in this specification to provide an overall understanding of the composition, function, operation, and application of the disclosed compositions and methods. It is understood that the various embodiments described and illustrated in this specification are non-limiting and non-exhaustive. Thus, the invention is not necessarily limited by the description of the various non-limiting and non-exhaustive embodiments disclosed in this specification. The features and characteristics illustrated or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be present in the prior art. Therefore, any such amendments comply with the requirements of 35 U.S.C. §§ 112(a) and 132(a). The various embodiments disclosed and described in this specification can comprise, include, consist of, or consist essentially of the features and characteristics as variously described in this specification.

Also, any numerical range recited in this specification is intended to include all sub-ranges of the same numerical precision subsumed within the recited range. For example, a range of 1.0 to 10.0 is intended to include all sub-ranges between (and including) the recited minimum value of 1.0 and the recited maximum value of 10.0, that is, having a minimum value equal to or greater than 1.0 and a maximum value equal to or less than 10.0, such as, for example, 2.3 to 6.6. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited in this specification. All such ranges are intended to be inherently described in this specification such that amending to expressly recite any such sub-ranges would comply with the requirements of 35 U.S.C. §§ 112(a) and 132(a).

Any patent, publication, or other disclosure material identified in this specification is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference into this specification. Any material, or portion thereof, that is said to be incorporated by reference into this specification, but which conflicts with existing definitions, statements, or other disclosure material set forth in this specification, is only incorporated to the extent that no conflict arises between that incorporated material and the existing disclosure material. Applicants reserve the right to amend this specification to expressly recite any subject matter, or portion thereof, incorporated by reference into this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise. Additionally, the grammatical conjunctions "and" and "or" are used herein according to their accepted usage. By way of example, "x and y" refers to "x" and "y". On the other hand, "x or y" refers to "x", "y", or both "x" and "y", whereas "either x or y" refers to exclusivity.

As herein described, an antimicrobial application system may be configured to recycle antimicrobial used in connection with food processing. The recycling may include recycling of antimicrobial applied to items associated with food processing for subsequent application of the recycled antimicrobial to items associated with food processing. The antimicrobial application system may include an antimicrobial application unit and a recycle unit. An initial, dilute antimicrobial composition may be prepared and the concentration of the antimicrobial may be controlled automatically by a control unit. The control unit may include or be operatively controllable by a processor. The processor may be configured to access a data storage medium having stored therein instructions executable by the processor to perform one or more operations of the antimicrobial application system. The antimicrobial composition may be provided to the antimicrobial application unit and applied to work pieces, such as raw poultry carcasses. After application to the work pieces, the antimicrobial composition may flow to a recycle tank of the recycle unit. The concentration of the antimicrobial in the antimicrobial composition flowing to the recycle tank may be monitored manually or by the system. Additional antimicrobial may be automatically added if the concentration of the antimicrobial in the antimicrobial composition falls below a desired amount. All or a portion of the antimicrobial composition may be periodically diverted to a capture tank and selective removal of the antimicrobial composition from the composition. The removed antimicrobial and remaining composition are then disposed of in appropriate manners. The antimicrobial is preferably a quaternary ammonium compound, an alkylpyridinium chloride, or cetylpyridinium chloride.

In various embodiments, the antimicrobial application system may be configured to perform or achieve one or more of the following: reduction of raw material consumption without sacrificing safety; providing for periodic, batch style separation and disposal of spent antimicrobial; automatically monitor and maintain a desired composition of the antimicrobial composition to be recycled; provide for improved recapture and return of an antimicrobial composition applied to work pieces; automatically compensate for additional liquids passing from wetted work pieces to the recycled antimicrobial composition; capable of providing continuous, real-time monitoring and control of the composition of an antimicrobial composition; reduce waste leaving the system and waste disposal costs associated therewith; provide a safe waste stream that may be safely drained into a wastewater system; increase the flexibility and advantages of the spray application systems and spray cabinets disclosed in U.S. Pat. No. 6,742,720 and in PCT Application Serial Number PCT/US03/35933; effectively apply, capture, and reapply a solution that is prone to foaming; provide increased flexibility in positioning and utilization of spray nozzles; handle large fluctuations in processing requirements; is relatively easy to install, clean, and maintain; and provide a simple, reliable method of monitoring and controlling the composition of an antimicrobial to be recycled, even when the antimicrobial contains impurities.

Referring to FIG. 1, the reference numeral 10 refers in general to an antimicrobial application system according to various embodiments. The antimicrobial application system 10 generally comprises an antimicrobial application unit 12 and a recycle unit 14, and may include a capture unit 15.

The antimicrobial application unit 12 may take any number of configurations. In the preferred embodiment, the antimicrobial application unit 12 takes the general form of one of the embodiments of a spray application system as disclosed in U.S. Pat. No. 6,742,720. One possible exception is that the liquid barriers described in U.S. Pat. No. 6,742,720 are not used in a preferred embodiment. A conveyor 16 passes through a housing 18 for moving workpieces 20, such as raw poultry, through the housing 18. As described in more detail below, a drip tray or pan 22 extends downstream of the housing 18, disposed below the conveyor 16 and the workpieces 20 carried thereby. Examples of spray application systems that might be used in connection with the present embodiments are discussed in detail in U.S. Pat. No. 6,742,720 and will not be discussed in more detail here. It is of course understood that the antimicrobial application unit 12 is not limited to those embodiments or to spray application systems in general. The antimicrobial application unit 12 may apply a composition such as an antimicrobial composition to any number of different kinds and types of workpieces 20 in any number of different ways. Methods of application used by such an application unit 12 may include but are not limited to spraying, misting, fogging, immersing, pouring, dripping, and combinations thereof. It is understood that the system 10 may be used to treat a wide variety of different workpieces 20, including but not limited to meat, poultry, fish, fresh and salt water seafood, fruits, vegetables, other foodstuffs, animals, food packaging, and items and surfaces related to food or food processing. It is also understood that the workpieces 20 may be live, dead, raw, hide-on, carcass, pieces, cooked, prepared, processed, partially processed, ready to eat, or ready to cook. It is further understood that the system 10 may be used to treat workpieces 20 completely unrelated to food or food processing items.

Figure 3:
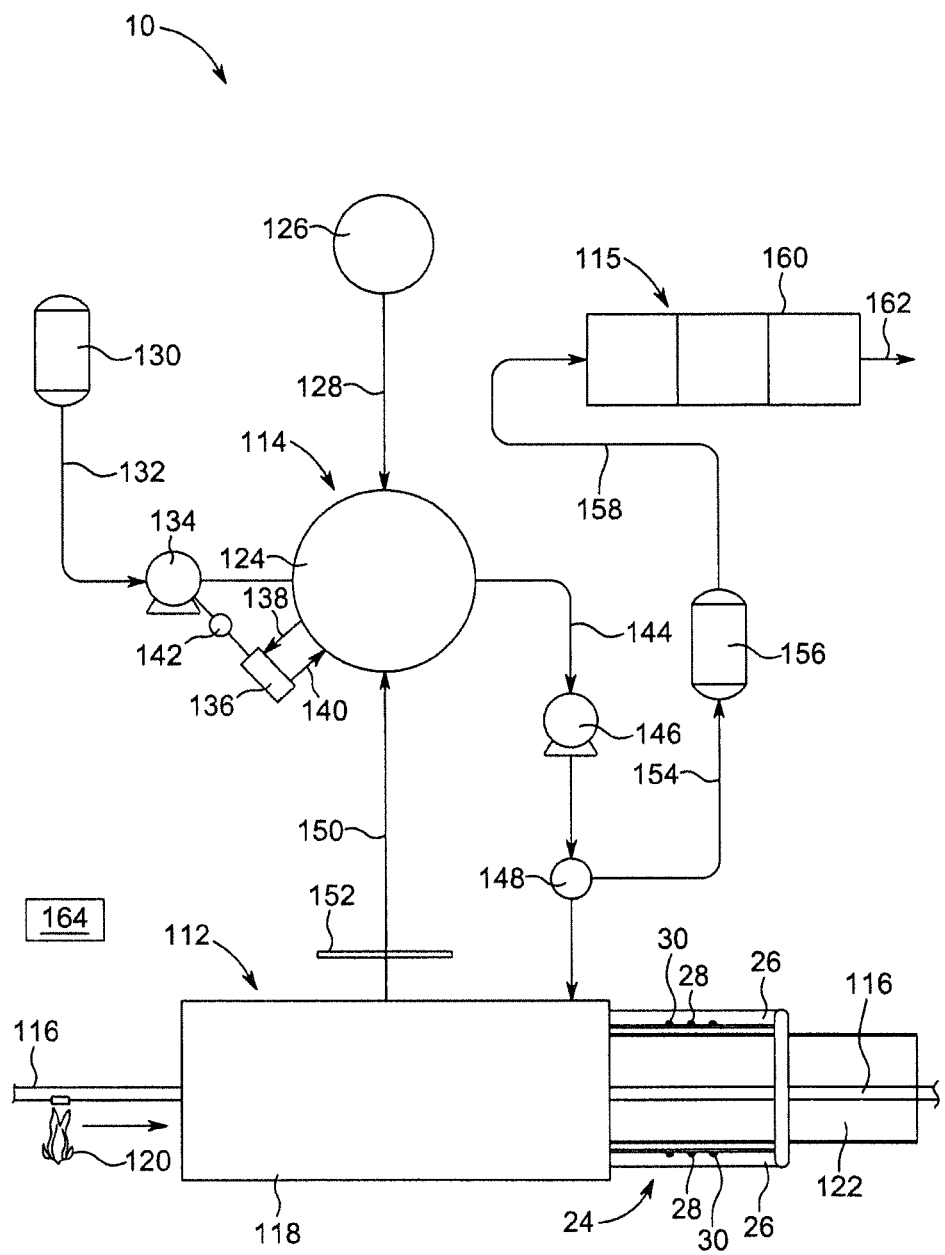
FIG. 3 is a schematic view of an antimicrobial application system according to various embodiments described herein.

A rigid member 24, such as stainless steel tubing, is affixed to the housing 18, preferably at a downstream end of the housing 18. As best seen in FIG. 3, the rigid member 24 has parallel arms 26 that are aligned on opposite sides of the conveyor line 16. A series of matching openings 28 are provided in each arm 26 for housing counters or sensors. Protective lenses 30 provide watertight seals, preferably NEMA 4 seals, to protect the counters from damage that might otherwise occur under the harsh washdown conditions to which the systems 10 are routinely subjected. Three counters are preferably provided in series. As best seen in FIG. 1, the arms 26 are disposed so that the counters are aligned to detect the presence or absence of workpieces 20. The use of three counters provides redundancy and increases accuracy. In that regard, the counters are operably connected to a controller such as a central control unit 32 or 164, and the counts taken by the three counters are continuously compared. If one counter provides a reading or count that differs from that provided by the other two, the central control unit 32 or 164 will typically be programmed to disregard the reading of the inconsistent counter and rely instead upon the readings of the other two counters. The logic and interpretation of the different readings may of course be modified in any number of ways.

The recycle unit 14 dilutes a concentrated antimicrobial composition or solution to obtain a dilute antimicrobial composition or solution and provides the dilute antimicrobial solution to the antimicrobial application unit 12. An antimicrobial source, such as a supply tank 34, is connected to the housing 18 via antimicrobial supply line or conduit 36. A chemical feed pump 38 is disposed in antimicrobial supply line 36. The pump 38 is operably connected to a controller 40 for reasons to be described below. The antimicrobial preferably comprises a quaternary ammonium compound, more preferably comprises an alkylpyridinium chloride, and most preferably comprises cetylpyridinium chloride. More particularly, the concentrated antimicrobial solution preferably comprises a concentrated solution of a quaternary ammonium compound as described in U.S. patent application Ser. No. 09/494,374, filed on Jan. 31, 2000 by Compadre et al. The disclosure of U.S. patent application Ser. No. 09/494,374 (Compadre et al.) is incorporated herein by reference. The concentrated solution preferably comprises an antimicrobial and a solubility enhancing agent, and the solubility enhancing agent preferably comprises propylene glycol. The quaternary ammonium compound is preferably present in the concentrated solution in a weight percent of approximately 40%, and the solubility enhancing agent is preferably present in the concentrated solution in a weight percent of approximately 60%. It is of course understood that any number of different antimicrobials and solubility enhancing agents may be used, and the concentrated and dilute solutions may have any number of different components and compositions, including but not limited to the components and compositions of the concentrated and dilute solutions disclosed in U.S. patent application Ser. No. 09/494,374 (Compadre et al.). Concerns of adulteration, contamination, or cross-contamination are eliminated or alleviated because of the broad-spectrum efficacy of the preferred antimicrobial solutions and because of the filtration and automatic concentration measures.

One or more recycle tanks 42 are provided. A return line or conduit 44 extends between the housing 18 and the recycle tank 42 for passing liquid from the housing 18 to the tank 42. Multiple return lines 44 may be used to connect multiple antimicrobial application units 12 to the recycle tanks 42. A filter 46 is disposed in the housing 18 or in the return line 44. The filter 46 is preferably a wire mesh filter, such as a 100 mesh filter, sized to capture visible particulate matter in the effluent from the antimicrobial application unit 12. Visible particulate matter in the effluent will typically be minimal because of upstream washing that will typically be performed on the workpieces 20. First and second filters 48 and 50 are associated with each tank 42 and are disposed between the tank 42 and a system pump 52 to provide for parallel flow between the tank 42 and the system pump 52. Valves 54 or other means are provided for selectively directing liquid passing from the tank 42 to the system pump 52 through either the first filter 48 or the second filter 50. This allows the system 10 to continue operating while one of the filters 48 or 50 is being cleaned, replaced, or repaired. A three-way valve 56 is disposed in conduit 58 for reasons to be discussed below. A purge or capture line 60 passes from the valve 56 to the capture tank 62. A capture pump 64 is disposed in capture line 60. Although the recycle tank 42 may include an impeller or some other stirring or agitation means, no such stirring or agitation means is used in the preferred embodiment. A feed line 66 passes from the system pump 52 to the housing 18 and is connected to one or more sprayers 68. Multiple feed lines 66 may be used, or the feed line 66 may be branched or divided, if desired, to connect the recycle tank 42 to multiple antimicrobial application units 12. A bypass conduit 70 having a relief valve 72 is disposed in the feed line 66. A diverting line 74 is also disposed in the feed line 66. The diverting line 74 is connected to a dilution pump 78 and has a pressure regulator 80 disposed therein.

A source of potable water 82, such as tap water, is connected to the recycle tank 42 via water supply line or conduit 84. A diverting line 86 is also disposed in water supply line 84. The diverting line 86 is connected to a dilution pump 88 and has a pressure regulator 90 disposed therein. The pressure regulators 80 and 90 preferably regulate the pressure in lines 74 and 86 to a pressure lower than the pressures in lines 66 and 84 and preferably regulate the pressure in lines 74 and 86 down to approximately 15 psig. The dilution pumps 78 and 88 are electrically interlocked to provide for matched, stroke for stroke pumping action. The dilution pumps 78 and 88 are also sized to provide for a desired, fixed dilution ratio. The dilution ratio is preferably less than or equal to approximately 1 part dilute composition to 1 part water, is more preferably less than or equal to approximately 1 part dilute composition to 30 parts water, and is most preferably less than or equal to approximately 1 part dilute composition to 60 parts water. Conduits 92 and 94 exit the dilution pumps 78 and 88 and are disposed to route liquids from the dilution pumps 78 and 88 to a static mixer 96. The static mixer is preferably an inline, auger style static mixer.

A sensor 98 is disposed at the discharge end of the static mixer 96. In the preferred embodiment, the sensor 98 is an ultraviolet light spectrophotometer or UV spec sensor. Of course it is understood that any number of different types of sensors 98 may be used, including but not limited to infrared, visible light, or ultraviolet sensors. The sensor 98 is capable of detecting the concentration of the antimicrobial in the solution exiting the static mixer 96. The controller 40 operably connects the sensor 98 to the chemical feed pump 38. The controller 40 is capable of receiving a signal from the sensor 98 and sending a corresponding on/off signal to the chemical feed pump 38. A discharge line 100 passes from the sensor 98 to the capture or purge tank 62.

A siphon 102 is disposed in the capture tank 62 and is connected to a drain line 104. The drain line 104 passes from the capture tank 62 to an antimicrobial separation unit 106. The antimicrobial separation unit 106 preferably comprises one or more filters 108 or filter units each comprising a container dimensioned to retain a volume of filter material, such as disposable carbon filters, that selectively remove the antimicrobial from the composition. An intermediate filter line 109 connects the filters 108. A disposal line 110 exits the antimicrobial separation unit 106 for disposing of water and any other components remaining after the antimicrobial is selectively removed. It is understood that a separation unit 106 may or may not be used and that any number of different separation methods may be used. It is also understood that filters 108 may be disposable or reusable.

The central control unit 32 is used to control the entire system 10. The central control unit 32 may perform various tasks or functions in association with operation of the system 10. For example, the central control unit 32 may operatively associated with system processes to collect, process, and/or communicate data indicative of operational states, system conditions, triggering events, component functions, events, or other like data. One or more sensors, such as sensor 98, may be operatively associated with the central control unit 32 to detect and to provide signals indicative of system operation conditions or conditions in connection with operation of the system 10, for example. In one embodiment, the central control unit 32 is programmed to activate, deactivate, or modulate system pumps or valves, to receive, transmit, and/or process data signals in communication with one or more components of the system 10, or to process or analyze data communicated from one or more sensors operatively associated with various units of the system. For example, the sensor 98 or another sensor may be configured to detect contaminants or other aspects of fluid composition associated with the fluid recycled through the system 10. The central control unit may include one or more processors or computer systems programmed with software, firmware, or other computer-executable instructions to perform the various functions of the control module. The central control unit 32 may be operatively associated with one or more data transmission devices which may receive and/or store data received or processed by the central control unit 32. In certain embodiments, the central control unit 32 may communicate signals to one or more indicators which reflect the activity or function of different aspects of the system 10. For example, one such indicator may include a warning light, or an alert graphical display associated with a local or remote plant monitor.

In operation, a dilute antimicrobial solution will typically be prepared and used for one spray cycle that will typically last for one day. The dilute antimicrobial solution will then be discarded, disposed of, or removed from the system 10 for further processing. It is of course understood that the spray cycle may be of any number of different durations. It is also understood that the system 10 may be operated in batch mode, in steady-state mode, or in any number of different types or combinations of modes of operation. A new spray cycle will typically begin each morning with an empty and clean recycle tank 42 and an empty and clean capture tank 62. Before the antimicrobial application unit 12 is activated, and before the system pump 52 is turned on, the dilute antimicrobial solution is prepared. In that regard, a desired amount of tap water is fed to the recycle tank 42. The recycle tank 42 is preferably filled to approximately one third to approximately one half of its capacity with potable water. The concentration pump 38 is activated to feed the concentrated antimicrobial composition to the housing 18, where it drains through return conduit 44, and to the recycle tank 42, until a predetermined amount of the concentrate composition is provided. The concentrate composition combines with the water in the recycle tank 42 to form a dilute solution of the desired concentration. The desired ranges of the concentration of antimicrobial in dilute solution include but are not limited to the concentration ranges of the antimicrobial in the dilute solutions disclosed in U.S. patent application Ser. No. 09/494,374 (Compadre et al.).

Once the desired concentration is obtained in the recycle tank 42, the system pump 52 is activated, and the dilute solution is supplied to the antimicrobial application unit 12. The dilute solution provided to the antimicrobial application unit 12 is not potable. Still, contamination or cross-contamination of the workpieces 20 is not a concern because of the safety and broad spectrum efficacy of the dilute antimicrobial solution used. The recycle unit 14 supplies the dilute antimicrobial solution to the antimicrobial application unit or units 12 at any number of different flow rates and pressures. These flow rates and pressures may include, but are not limited to, the flow rates and pressures discussed in U.S. Pat. No. 6,742,720. The bypass conduit 70 and relief valve 72 route a portion of the dilute composition to a lower portion of the housing 18 so that it does not pass through the sprayers 68 and is not applied to the workpieces 20. The ratio of dilute composition passing through the bypass conduit 70 versus passing to the sprayers 68 will typically be greater than or equal to approximately 1:1 and will more typically be greater than or equal to approximately 2:1. The dilute composition passing through the bypass conduit 70 provides for improved mixing of the captured composition and any concentrate composition that might be added. The use of the bypass conduit 70 and relief valve 72 provides greater flexibility in providing dilute composition to sprayers 68 at or within desired pressure ranges. The use of the bypass conduit 70 and relief valve 72 also makes it easier to continue to provide dilute composition to the sprayers 68 at consistent pressure as additional spray application units 12 are brought online or taken offline and regardless of the number of spray application units 12 that are online.

Once the recycle unit 14 is supplying the dilute antimicrobial solution to the antimicrobial application unit 12, the workpieces 20 to be processed, such as raw poultry, are moved by the conveyor 16, through the housing 18, and the dilute antimicrobial solution is applied to the workpieces 20, such as by spraying. The portion of the dilute antimicrobial solution that does not adhere to the workpieces 20 collects in a drain and is returned via return line 44, through filter 46, and to the recycling tank 42 for reuse. The length of the drip tray 22 is selected so that it will catch drops from workpieces 20 exiting the housing 18 for approximately 1 minute after the workpieces 20 exit the housing 18. This enhances the recovery of the dilute antimicrobial solution and reduces downstream losses. Although not preferred, liquid barriers such as water spray curtains may be used in the housing 18. Also, the workpieces 20 may be wet from upstream washing, so additional water may enter the recycle tank 42, decreasing the concentration of the antimicrobial in the dilute solution.

It is desirable to avoid concentration spikes in the dilute composition, particularly in the dilute composition exiting the sprayers 68 and passing through the diverting line 74 for routing to sensor 98. Accordingly, steps are taken to insure thorough mixing of the dilute composition being recycled between the recycle unit 14 and the antimicrobial application unit 12. This is one reason why the concentrate supply line 36 routes the concentrated antimicrobial solution to the housing 18 rather than directly to the recycle tank 42. By the time the concentrate composition mixes with dilute compositions from the sprayers 68 and from the bypass line 70, passes through return line 44, filter 46, recycle tank 42, filter 48 or 50, and system pump 52, the resultant liquid is thoroughly mixed and has a relatively uniform composition.

A preferred sensor 98, such as a spectrophotometer, is typically used to measure very low concentrations of a component in a composition. It is therefore important to provide a liquid that has not only has a relatively uniform composition but also a very low concentration of the antimicrobial or component to be measured. Often, it will not be practical or feasible to obtain accurate, reliable readings for the antimicrobial at the concentration ranges typically found in the recycle tank 42. Diluting the composition before taking a concentration reading will offer greater flexibility in the selection of a sensor 98 for monitoring the concentration of the antimicrobial. Samples of the composition exiting the recycle tank 42 are therefore taken and further diluted, to yield further diluted compositions in which the antimicrobial is present within a concentration range that is readily and accurately measured by the sensor 98. The dilution ratio of the dilution pumps 78 and 88 is selected to provide the desired degree of dilution, such as within the ranges discussed above. The pumps 78 and 88 are set on a timer to take samples at a set interval, each sample being taken for a set duration of time. It is understood that the concentration may be monitored at any number of different intervals and for any number of different durations and that the concentration may be continuously monitored. The electrically interlocked pumps 78 and 88 provide the dilute composition and water in the desired fixed ratio to further dilute the dilute composition. Using electrically interlocked pumps at a desired, fixed dilution ratio simplifies controls needed to operate the system 10. It is of course understood that the pumps need not be interlocked, the dilution ratio need not be fixed, and any number of different methods may be used to select, control, and adjust the dilution ratio as desired.

The dilute composition and water are combined and passed through the static mixer 96 to provide for thorough mixing, further reducing the risk of concentration spikes as the liquid passes the spectrophotometer 98. The spectrophotometer 98 senses the concentration of the antimicrobial in the passing liquid. The sensor 98 is operably connected to the controller 40. Accordingly, if the sensor 98 detects that the concentration of antimicrobial falls below a desired amount, the controller 40 activates the chemical feed pump 38 to add more of the concentrated antimicrobial solution into the housing 18 and to bring the concentration of the antimicrobial in the dilute antimicrobial solution back up to the desired level. The system 10 can be configured to allow the potable water to be controlled in this fashion as well, but it is unlikely that there will be a need to add make-up water.

It is undesirable to route the highly diluted liquid that passes the sensor 98 back into the recycle tank 42, so it is routed to the capture tank 62. The siphon 102 in the capture tank 62 allows the liquid to collect in the capture tank 62, until the liquid reaches a desired level. When the liquid in the capture tank 62 reaches the desired level, the siphon 102 empties the capture tank 62, passing the liquid through conduit 104 and to the disposable carbon filters 108 of the antimicrobial separation unit 106. The disposable filters 108 capture the antimicrobial to selectively remove the antimicrobial from the solution. Using the siphon 102 reduces or eliminates channeling problems that might otherwise arise if the liquid were allowed to continuously drip from the capture tank 62 onto the carbon filters 108.

At the end of the spray cycle, such as at the end of a shift or a day or other chosen period of time, the valve 56 is actuated to divert the dilute antimicrobial solution received from the recycle tank 42 to the capture pump 64. The capture pump 64 empties the recycle tank 42 and passes the dilute antimicrobial solution to the capture tank 62. When the liquid reaches a desired level in the capture tank 62, the siphon 102 routes the liquid through conduit 104 and to the disposable carbon filters 108 of the antimicrobial separation unit 106. The disposable filters 108 capture the antimicrobial to selectively remove the antimicrobial from the solution. When the antimicrobial impregnated disposable filters 108 are spent, they are then disposed of in an appropriate manner, such as by incineration or disposal at an approved landfill. The remaining, relatively antimicrobial-free liquid is then disposed of in an appropriate manner, such as by being drained into a wastewater system of a plant. The frequency with which the system 10 will need to be purged will depend upon any number of factors, such as the number of workpieces 20 to be processed by the antimicrobial application unit 12 and the volume of the dilute antimicrobial solution required to charge the system 10 at the beginning of a spray cycle. A periodic purge of the system 10 will typically be used.

An alternate embodiment of the antimicrobial application system 10 is disclosed in FIG. 3. The antimicrobial application system 10 of the alternate embodiment also generally comprises an antimicrobial application unit 112 and a recycle unit 114 and will typically include a capture unit 115.

The antimicrobial application unit 112 may take any number of configurations. For example, the antimicrobial application unit 112 may take the general form of one of the embodiments of a spray application system as disclosed in U.S. patent application Ser. No. 10/001,896. In the preferred embodiment, spray containment barriers are not used. A conveyor 116 passes through a housing 118 for moving workpieces 120, such as raw poultry, through the housing 118. As described in more detail below, a drip tray or pan 122 extends downstream of the housing 118, disposed below the conveyor 116 and the workpieces 120 carried thereby.

The spray application systems are discussed in detail in U.S. Pat. No. 6,742,720 and will not be discussed in more detail here. It is of course understood that the antimicrobial application unit 112 is not limited to those embodiments or to spray application systems in general. The antimicrobial application unit 112 may apply an antimicrobial to any number of different types of workpieces 120 in any number of different conventional ways. Methods of application used by such an antimicrobial application unit 112 may include but are not limited to spraying, misting, fogging, immersing, pouring, dripping, and combinations thereof. It is understood that the system 10 may be used to treat a wide variety of different workpieces 120, including but not limited to meat, poultry, fish, fruits, vegetables, other foodstuffs, animals, food packaging, and items and surfaces related to food or food processing. It is also understood that the workpieces 120 may be live, dead, raw, cooked, prepared, processed, partially processed, or ready to eat. It is also understood that the system 10 may be used to treat workpieces 120 completely unrelated to food or food processing items.

The recycle unit 114 dilutes a concentrated antimicrobial composition to obtain a dilute antimicrobial composition and provides the dilute antimicrobial composition to the antimicrobial application unit 112. A recycle tank 124 is provided. The recycle tank 124 may include an impeller or some other stirring or agitation means. A source of potable water 126, such as tap water, is connected to the recycle tank 124 via water supply line 128. Similarly, an antimicrobial source, such as a supply tank 130, is connected to the recycle tank 124 via antimicrobial supply line 132. The antimicrobial preferably comprises a quaternary ammonium compound, more preferably comprises an alkylpyridinium chloride, and most preferably comprises cetylpyridinium chloride. More particularly, the concentrated antimicrobial composition preferably comprises a concentrated composition of a quaternary ammonium compound as described in U.S. patent application Ser. No. 09/494,374, filed on Jan. 31, 2000 by Compadre et al. The disclosure of U.S. patent application Ser. No. 09/494,374 (Compadre et al.) is incorporated herein by reference. The concentrated composition preferably comprises an antimicrobial and a solubility enhancing agent, and the solubility enhancing agent preferably comprises propylene glycol. The quaternary ammonium compound is preferably present in the concentrated composition in a weight percent of approximately 40%, and the solubility enhancing agent is preferably present in the concentrated composition in a weight percent of approximately 60%. It is of course understood that any number of different antimicrobials and solubility enhancing agents may be used, and the concentrated and dilute compositions may have any number of different components and compositions, including but not limited to the components and compositions of the concentrated and dilute compositions disclosed in U.S. patent application Ser. No. 09/494,374 (Compadre et al.). Concerns of contamination or cross-contamination are eliminated or alleviated because of the broad spectrum efficacy of the preferred antimicrobial compositions.

A chemical feed pump 134 is disposed in antimicrobial supply line 132. A sensor 136 is connected to the recycle tank 124 via lines 138 and 140. In the preferred embodiment, the sensor is an ultraviolet light photospectrometer or UV spec sensor. It is of course understood that any number of different sensors and any number of different light sensors may be used. For example, the light sensor may use light having wavelengths that fall in any number of different ranges, including but not limited to ultraviolet light, visible light, infrared light, and combinations thereof. Of course it is understood that any number of different types of sensors 136 may be used, including but not limited to infrared, visible light, or ultraviolet sensors. The sensor 136 is capable of detecting the concentration of the antimicrobial in the composition in the recycle tank 124. A controller 142 operably connects the sensor 136 to the chemical feed pump 134. The controller 142 is capable of receiving a signal from the sensor 136 and sending a corresponding on/off signal to the chemical feed pump 134. A feed line 144 exits the recycle tank 124, passes through the system pump 146, through a valve 148, and connects to the antimicrobial application unit 112. Multiple feed lines may be used, or the feed line 144 may be branched or divided, if desired, to connect the recycle tank 124 to multiple antimicrobial application units. The valve 148 is preferably a three-way valve. A return line 150 exits the antimicrobial application unit 112, passes through a filter 152, and connects to the recycle tank 124. Multiple return lines may be used to connect multiple antimicrobial application units to the recycle tank 124. The filter 152 is preferably a wire mesh filter sized to capture visible particulates in the effluent from the antimicrobial application unit 112. Visible particulates in the effluent will typically be minimal because of upstream washing that will typically be performed on the workpieces 120. A capture line 154 passes from the valve 148 to a capture tank 156. A drain line 158 passes from the capture tank 156 to an antimicrobial separation unit 160. The antimicrobial separation unit 160 preferably comprises one or more disposable filters selected to separate the antimicrobial from water. A disposal line 162 exits the antimicrobial separation unit 160 for disposing of water after the antimicrobial is removed. A central control unit 164 is used to control the entire system 10 and may be similar to the central control unit 32.

In operation, a dilute antimicrobial composition will typically be prepared and used for one spray cycle that will typically last for one day. The dilute antimicrobial composition will then be discarded, disposed of, or removed from the system 10 for further processing. Accordingly, each spray cycle, typically beginning each morning, begins with an empty and clean recycle tank 124 and an empty and clean purge or capture tank 156. Before the antimicrobial application unit 112 is activated, and before the system pump 146 is turned on, the dilute antimicrobial composition is prepared. In that regard, a desired amount of tap water is fed to the recycle tank 124. The recycle tank 124 is preferably filled to approximately one third to approximately one half of its capacity with potable water. The central control unit 164 activates the sensor 136 so that liquid from the recycle tank 124 passes through the sensor 136. The sensor 136 initially detects the absence of antimicrobial (no absorbance at 260 nm), so the controller 142 activates the chemical feed pump 134 to begin metering the concentrated antimicrobial composition into the recycle tank 124. When the concentration of the antimicrobial in the dilute composition in the recycle tank 124 reaches a desired level, the sensor 136 and, in turn, the controller 142 turn off the chemical feed pump 134. The desired ranges of the concentration of antimicrobial in dilute composition include but are not limited to the concentration ranges of the antimicrobial in the dilute compositions disclosed in U.S. patent application Ser. No. 09/494,374 (Compadre et al.). Once the desired concentration is obtained in the recycle tank 124, the system pump 146 is activated, and the dilute composition is supplied to the antimicrobial application unit 112. The dilute composition provided to the antimicrobial application unit 112 is not potable. Still, contamination or cross-contamination of the workpieces 120 is not a concern because of the safety and broad spectrum efficacy of the dilute antimicrobial composition used. The recycle unit 114 supplies the dilute antimicrobial composition to the antimicrobial application unit or units 112 at any number of different flow rates and pressures. These flow rates and pressures may include, but are not limited to, the flow rates and pressures discussed in U.S. Pat. No. 6,742,720.

Once the recycle unit 114 is supplying the dilute antimicrobial composition to the antimicrobial application unit 112, the workpieces 120 to be processed, such as raw poultry, are moved by the conveyor 116, through the housing 118, and the dilute antimicrobial composition is applied to the workpieces 120, such as by spraying. The portion of the dilute antimicrobial composition that does not adhere to the workpieces 120 collects in a drain and is returned via return line 150, through filter 152, and to the recycling tank for reuse. The length of the drip tray 122 is selected so that it will catch drops from workpieces 120 exiting the housing 118 for approximately 1 minute after the workpieces 120 exit the housing 118. This enhances the recovery of the dilute antimicrobial composition and reduces downstream losses. Water spray curtains may be used in the application chamber, and the workpieces 120 may be wet from upstream washing, so additional water will typically enter the recycle tank 124.

The sensor 136 continuously monitors the concentration of the antimicrobial in composition in the recycling tank. If the concentration falls below a desired amount, the sensor 136 activates the chemical feed pump 134 to add more of the concentrated antimicrobial composition and to bring the concentration of the antimicrobial in the dilute antimicrobial composition back up to the desired level. The system 10 can be configured to allow the tap water to be controlled in this fashion as well, but it is unlikely that there will be a need to add water. The dilute antimicrobial composition is thereby used repeatedly to treat any number of units of the workpieces 120 being processed.

At the end of the spray cycle, such as at the end of a shift or a day or other chosen period of time, the valve 148 is actuated to divert the dilute antimicrobial composition received from the system pump 146 through capture line 154 to the purge tank 156. The liquid in the purge tank 156 is gravity fed through the drain line 158 to the disposable filters of the antimicrobial separation unit 160. The disposable filters capture the antimicrobial to separate the antimicrobial from the composition. The antimicrobial impregnated filters are then disposed of in an appropriate manner, such as by incineration or disposal at an approved landfill. The remaining, relatively antimicrobial-free liquid is then disposed of in an appropriate manner, such as by being drained into a wastewater system of a plant. The frequency with which the system 10 will need to be purged will depend upon any number of factors, such as the number of workpieces 120 to be processed by the antimicrobial application unit 112 and the volume of the dilute antimicrobial composition required to charge the system 10 at the beginning of a spray cycle. A periodic purge of the system 10 will be used.

Figure 2:
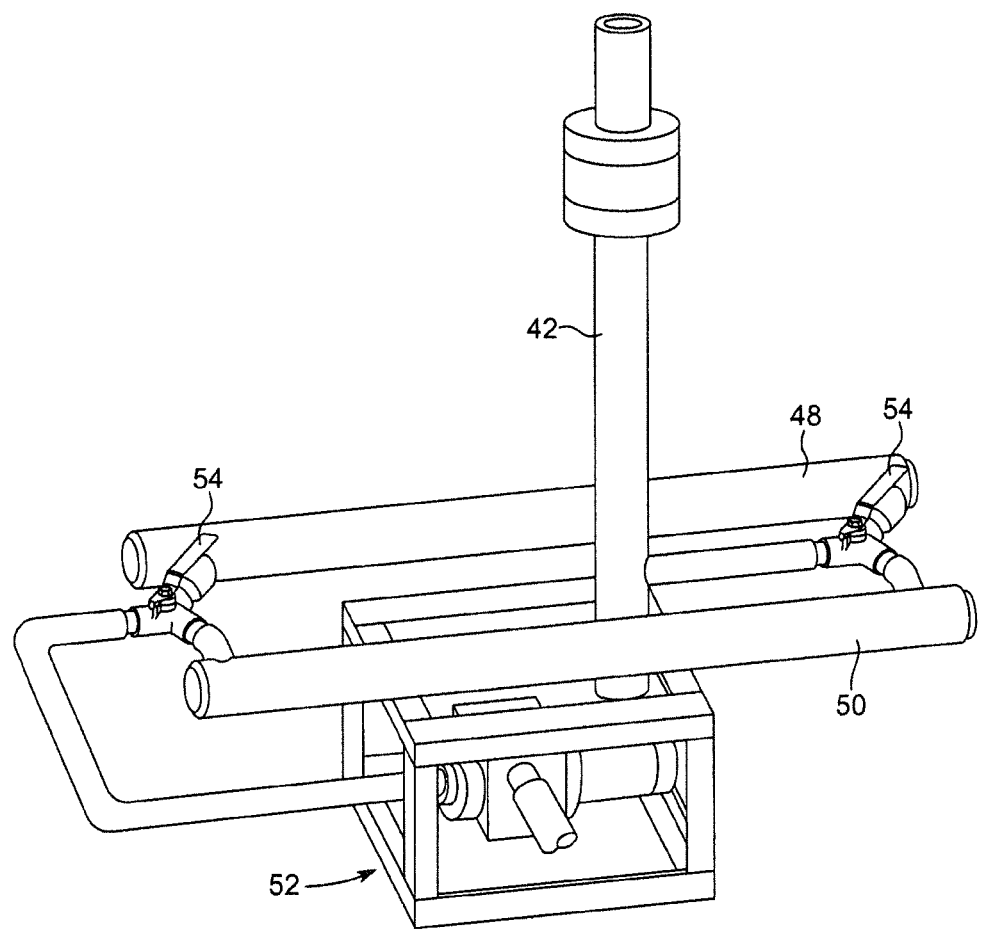
FIG. 2 is a side elevation view of a portion of a recycle unit according to various embodiments described herein.
Figure 4:
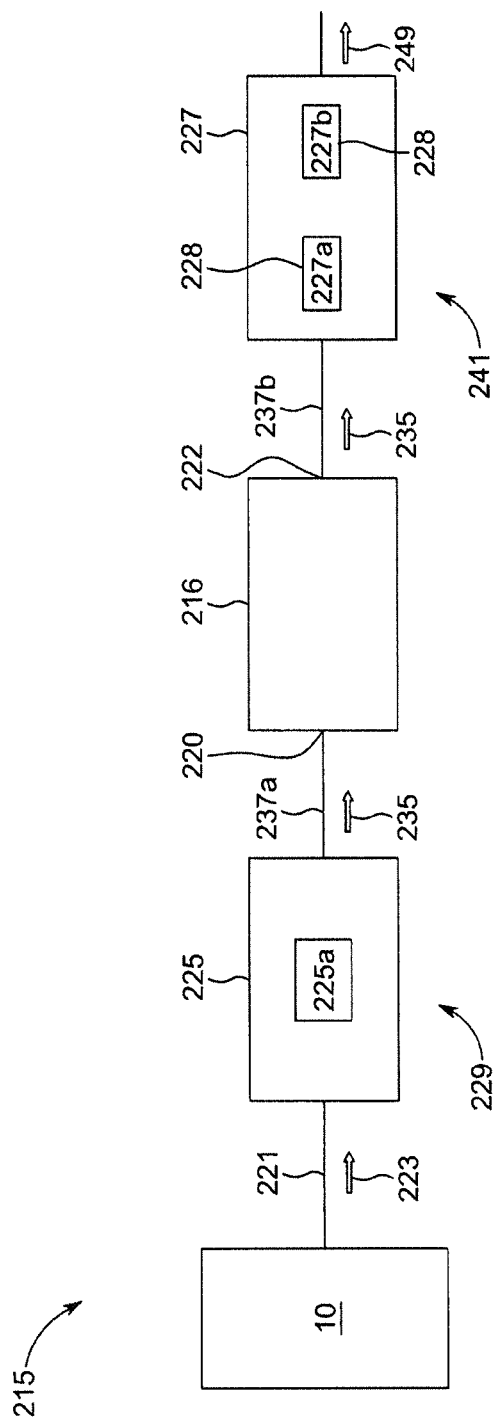
FIG. 4 is a schematic view of a capture unit according to various embodiments described herein.

FIG. 4 schematically illustrates another embodiment of a capture unit 215 including an upstream filter 225 and a downstream filter 227. The capture unit 215 may be configured for use with the embodiments of FIGS. 1-3, as described above, and may be configured to capture all or a portion of the antimicrobial component of the dilute antimicrobial solution. For example, at the end of a spray cycle, such as at the end of a shift or a day or other chosen period of time, the system 10 may be purged of dilute antimicrobial solution. The purging may include initiation of a capture sequence or transition to a capture mode that coordinates pump and valve operations to thereby direct the dilute antimicrobial solution to the capture unit 215. The central control unit 32, 164 may be programmed to sequentially or simultaneously activate or deactivate one or more system valves or otherwise operate a valve or valve apparatus in response to purge signal. The purge signal may be transmitted by user or associated with a programmed triggering condition, for example. Such triggering conditions may be associated with a condition of the dilute antimicrobial solution, an operational state of one or more units of the system, the occurrence of a predetermined event (e.g., number of workpieces processed or fixed period of time), and/or a variety of other potential triggering conditions or events. In addition to purging or turning over the system, the central control unit 32, 164 may coordinate transport of dilute antimicrobial solution to the capture unit 215 for processing and disposal as part of other system operations, which may include a programmed response to a triggering event, to, for example, dispose of diluted samples used for performing concentration measurements, to adjust the volume of dilute antimicrobial solution circulating through the system 10 from the recycle unit 14, 114, to partially turnover system fluids to address a low level contamination, or as otherwise desired.

In one configuration, during a purge of the system 10, the central control unit 32, 164 may coordinate opening or closing of one or more system valves, such as valves 56, 52, 80, or 90 and the powering on or off of one or more system pumps, such as capture pump 64 or feed pump 52, to empty dilute antimicrobial solution into one or more capture lines 221, such as capture lines 60, 100 or even discharge line 100, for processing and disposal of the effluent 223. For example, the dilute antimicrobial solution may be released or withdrawn from the recycle tanks 42, 124, application unit 12, or the static mixer 96, for example, and may be passed into the capture lines 60, 100, 221 toward the capture unit 215, which may be coupled to the capture line 221 to receive the effluent 223 for treatment and disposal. The capture unit 215 may be configured to process the effluent 223 and thereby capture or otherwise separate components of the effluent 223 to render it suitable for safe and cost-effective disposal as wastewater discharge. The components of the effluent 223 may include, without limitation, an antimicrobial component at various concentrations, a dilution component such as water, and may include additional components such as contaminants, visible particulates, debris, including organic or inorganic particles or byproducts, any of which may be collectively referred to as solid components herein.

The capture unit 215 may include various upstream and downstream filters 225, 227 configured to selectively interact or associate with one or more components of the effluent 223. In various embodiments, the filters 225, 227 may be configured to exploit one or more characteristics of the effluent 223 or its components to achieve a desired level of separation. For example, the filters 225, 227 may be configured to filter components of the effluent 223 based on size, charge, viscosity, consistency, molecular structure, molecular interactions, residues, forces, bonding, diffusion, or any other property or characteristic suitable for filtering such a component. The filters 225, 227 may include various filter layers, meshes, screens, selectively permeable membranes, packed columns, fluid beds, one or more stationary or mobile phases, adsorption media, etc. suitable to separate one or more of the components. For example, in at least one embodiment, the upstream filter 225 includes a solid separation unit 229 employing a screen filter 225a configured to separate solid components 231 from the effluent.

In various embodiments, the resultant upstream filtrate 235 released by the upstream filter 225 may be passed through a downstream capture line 237a to a capture tank 216. The upstream filtrate 235 may be resident in the capture tank 216 as described above or may pass directly through to the downstream capture line 237b. Controlling or monitoring passage of the upstream filtrate 235 toward the downstream filter 227 may be accomplished using a siphon 102, as described above with respect FIG. 1. A drain or valve may similarly be used to pass the upstream filtrate 235 into the downstream capture line 237b from the capture tank 216. In at least one embodiment, a pump may be fluidically coupled to the downstream capture line 237a, 237b to transport the upstream effluent filtrate 235 to the downstream filter 227.

The downstream filter 227 may include an antimicrobial separation unit 241 employing a series of at least two filters 227a, 227b such as columns, barrels, or drums packed with a filter material 243. In one such embodiment, the downstream filter 227 comprises an antimicrobial carbon filtration system including at least two carbon filter units 227a, 227b configured to retain a filter material 243 that includes activated carbon. The filter material 243 may be configured to adsorb the antimicrobial component 245 or other various components, such as undesirable contaminates from the effluent 223. A disposal line 247 may be coupled to the downstream filter 227 to pass the resultant downstream effluent filtrate 249 from the downstream filter 227 for disposal. In at least one embodiment, the capture unit 215 is configured to filter the effluent 223 such that the downstream effluent filtrate 249 is suitable for release as wastewater discharge into surface waters or municipal sewage treatment plants.

Figure 5:
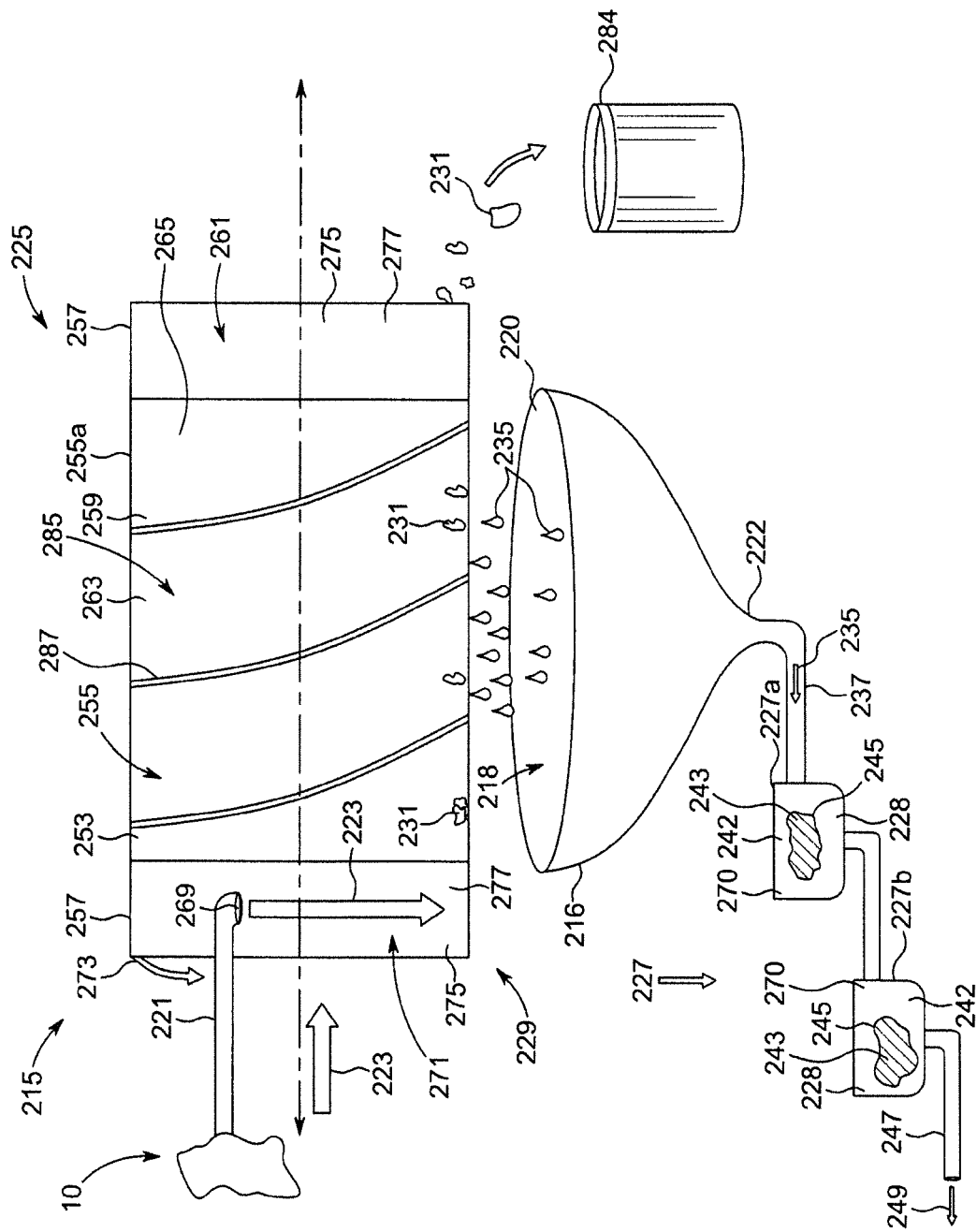
FIG. 5 is a semi-schematic view of a capture unit according to various embodiments described herein.

FIGS. 5-11 illustrate various configurations and features of the capture unit 215. As shown in FIG. 5, the capture unit 215 is configured to receive effluent 223 sent for capture to the capture unit 215. The capture unit 215 is configured to process the effluent 223 through the solid separation unit 229 and the antimicrobial separation unit 241. The solid separation unit 229 may include the upstream filter 225 and the antimicrobial separation unit 241 may include the downstream filter 227. It is to be understood that one or both of the upstream filter 225 and the downstream filter 227 may include multiple filters aligned in series or in parallel. The upstream filter 225 is configured to filter or separate the solid component 231 from the effluent 223 that may otherwise interfere with further transport or filtering of the effluent 223, e.g., by the downstream filter 227. The solid component 231 may include organic or inorganic materials that may have entered the dilute antimicrobial solution during the application process.

In various embodiments, the solid component 231 may include large particles, solids, solids associated with liquids, viscous liquids, fat, gelatinous material, debris, or other materials that may be filtered from the effluent via passage through the size restrictive screen filter 225a, shown in cross-section in FIG. 5. Notably, the solid component 231 separated from the effluent 223 by the upstream filter 225 could similarly accumulate on the upstream filter 225 thereby clogging the upstream filter 225 and limiting further transport of the effluent 223. Accordingly, the upstream filter 225 may be configured to separate the solid component 231 while also preventing the filtered solid component 231 from accumulating within the fluid path of the effluent 223 where it may otherwise clog the screen filter 225a and hinder further transport of the effluent 223. For example, in various embodiments, the upstream filter 225 may be positioned at an angle with respect to the direction of effluent flow or may include a series of traps configured to capture the solid component 231 filtered from the effluent 223. The upstream filter 225 may also be movable with respect to the flow path to prevent the solid component 231 separated by the filter 225*a* from blocking the flow of effluent 223 through the upstream filter 225. For example, the screen filter 225*a* may include a movable portion that may be slid or rotated from the fluid path such that retained solid component 231 is moved or rotated out of the flow path with the movable portion while another portion of the screen filter 225*a* is rotated into the flow path to filter the effluent 223.

The screen filter 225*a* may include a body 253 including a filter portion 255 positioned between ends 257 of the body. The body 253 may include an annular wall 259 defining a bore 261 that extends along a rotation axis "R" about which the filter portion 255 is configured to rotate as indicated by arrow 273. In various embodiments, the filter portion 255 may be constructed from strips of material patterned or cross-laid to form a plurality of holes or a mesh 263. The body 253 may also be constructed from a tube or drum through which perforations are formed to define the holes of the mesh 263 between an inwardly facing surface 265 and an outwardly facing surface 267 of the annular wall 259. The screen filter 265 is preferably coated with or formed of materials resilient to corrosion, e.g., anti-corrosives, stainless steel, synthetics, polymers, plastics, ceramics, etc. The holes of the mesh 263 may be dimensioned to obstruct passage of the solid component 231 having a minimum size or cross-section while allowing passage of the remaining effluent 223. In one preferred embodiment, the holes of the mesh 263 are sized to define cross-sections of about 0.0625 inches, however, the mesh 263 may include smaller or larger holes as well as fewer or additional holes, e.g., in consideration of the amount, size, or retention characteristics the solid components, rate or quantity of effluent, rotation rate or area of the filter portion, etc. In at least one embodiment, the mesh 263 of the filter portion 255 includes holes having different sized cross-sections.

Figure 6:
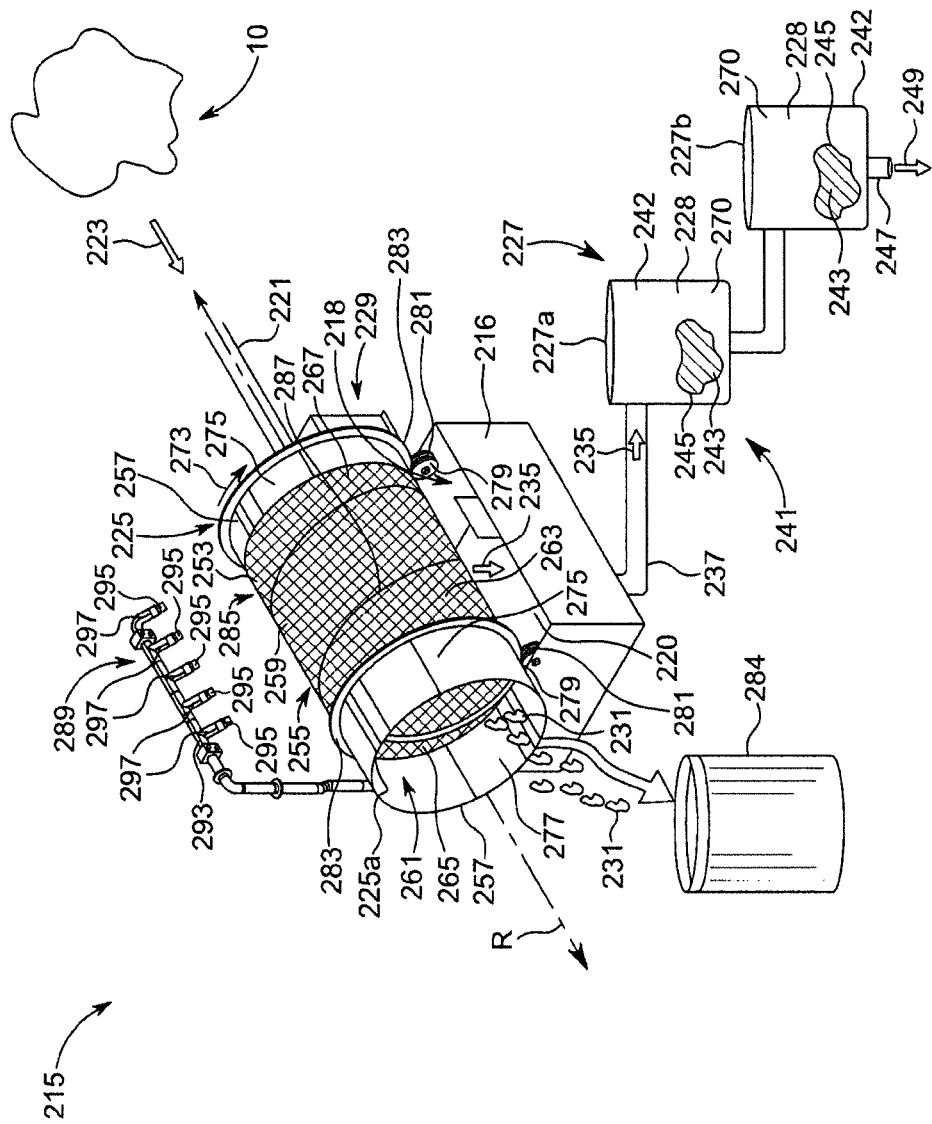
FIG. 6 is a semi-schematic view of a capture unit according to various embodiments described herein.

The upstream capture line 221 may include an outlet 269 adjacent to an end 257 of the screen filter 225*a* that is positioned to deliver effluent 223 into the bore 261. In at least one embodiment, the capture line 221 extends partially within the bore 261 and the outlet 269 may include a downspout directed toward or positioned to deliver the effluent 223 to a delivery region 271 that extends along an inwardly facing surface 265 of the annular wall 259. The delivery region 271 may include a band 275 positioned therealong defining a perimeter of the bore 261. The band may be formed of the same or a different material as the filter portion 255. The band 275 may have a solid or continuous inwardly facing surface 277 with respect to the bore 261. The inwardly facing surface 277 may be smooth to discourage accumulation of solid component 231 or from otherwise obstructing flow of effluent 223 from the delivery region 271 toward the filter portion 255. For example, the inwardly facing surface 277 may include a polished metallic surface. In at least one embodiment, the inwardly facing surface 277 of the band 275 may be textured to include grooves or projections. The grooves may be oriented to provide fluid paths for effluent 231 directed toward the filter portion or to breakup solid components 231. In one embodiment, the inwardly facing surface 277 may be treated or coated with a non-stick material to discourage accumulation of solid component 231. In some embodiments, the absence of holes defined in the inwardly facing surface 277 of the band 275 may allow effluent 223 to be delivered into the bore 261 onto the inwardly facing surface 277 while avoiding forcing accompanying solid component 231 onto the filter portion 255 where it may become lodged. As shown in FIGS. 5 and 6, the screen filter 225*a* may include bands 275 positioned at both ends 257 of the body 253. However, in at least one embodiment, the screen filter 225*a* includes only one band 275.

The screen filter embodiments shown in FIGS. 5 & 6 include inwardly facing surface 265 as well as the portion of the surface 265 that includes the inwardly facing surface 277 of the band portion 255 may be positioned along the horizontal substantially parallel. Upon delivery, the effluent 223 may be directed into the bore 261 such that it may pass to the filter portion 255, e.g., due to proximity to the filter portion 255 or sufficient momentum. In a further embodiment, a lip or ridge may be disposed at an end of the body 257 adjacent to the delivery region to prevent effluent 233 from exiting the bore 261 without passing onto the filter portion 255. In at least one embodiment, however, the inwardly facing surface 277 of the band 275 may be positioned at a raised angle with respect to the horizontal to urge the effluent 223 directed onto the inwardly facing surface 277 of the band 275 toward the filter portion 255 of the screen filter 225*a*. The raised angle may position the inwardly facing surface 277 to oppose the direction of effluent 233 flow with respect to its release from the outlet 269 to redirect the effluent 233 toward the filter portion 255 or may complement the general direction of flow of the effluent 233 toward the filter portion 255. In this or other embodiments, the body 253 of the screen filter 225*a* may be positioned at an angle with respect to the horizontal such that an end 257 is raised relative to the opposing end 257. The angle of the body 253 may further angle the inwardly facing surface of 265 extending along the filter portion 265. Accordingly, the outlet 269 of the upstream capture line 221 may be positioned to release effluent 223 onto the inwardly facing surface 277 at a high end of the band 275. In these or other embodiments, the outlet 269 may be angled to direct the effluent into the bore 261 or onto the inwardly facing surface 277 of the band 275 at a perpendicular, parallel, or other angle in-between.

As introduced above, the filter portion 255 of the screen filter 225*a* may be configured to rotate about a rotation axis R as generally identified by arrow 273. In at least one embodiment, the body 253 of the screen filter 225*a*, which may include the band 275, may also be configured to rotate with the filter portion 255. The rotation may be driven by any suitable mechanism configurable to rotate the filter portion 255 of the screen filter 225*a*, such as gears, pulleys, motors, etc. As shown, rotation of the filter portion 255 may be driven by rotation members 279 which may include engagement surfaces 281 such as gears positioned to operatively engage an engagement surface 281 of the screen filter 225*a* and thereon transmit rotation to the filter portion 255 or additional portions of the body 253.

As most clearly seen in the cross-section of the screen filter 225*a* provided in FIG. 5, in at least one embodiment, the screen filter 225*a* includes a screw 285 configured to urge effluent 223 through the bore 261. For example, the screw 285 may be configured to urge liquid portions of the effluent 223 along the inwardly facing surface 265 of the annular wall 259, such as the inwardly facing surface 277 of the band 275, toward the filter portion 255. The screw 285 may also be configured to urge solid components 231 along the annular wall 259 through the bore 261 toward a solids trap 284. The solids trap 284 may, for example, be located at an end 257 of the body 253 where solid components 231 may be released for disposal. The screw 285 may include a thread 287 protruding from the annular wall 259 toward the rotation axis R. The thread 287 may wrap around the annular wall 259 within the bore 261 between the ends 257 of the body 253 to form a helix therein. The thread 287 may be directionally oriented to complement the rotation of the filter portion 255 to direct separated solid components 231 toward an end 257 of the bore 261 where the solid components 231 may then be passed for disposal. For example, the thread 287 may wrap around the inwardly facing surface 265 in a clockwise or counterclockwise direction with respect to an end 257 of the body 253 to directionally urge solid components 231 toward or away from the end 257 of the body 253 as induced by the direction of rotation and location of the delivery region 265.

In various embodiments, the screen filter 225a may include or be configured for implementation with a cleaning unit 289, as most clearly seen in FIG. 6. In one form, the cleaning unit 289 may be used to clean one or more portions of the screen filter 225a, e.g., dislodge solid components 231 from the annular wall 259 or filter portion 255, provide additional lubrication to encourage passage of solid components 231 through the bore 261, discourage accumulation of solid components 231 on annular wall 259 or filter portion 255, etc. The cleaning unit 289 may be equipped with a scraper 291 configured to implement cleaning operations of the cleaning unit 289. The scraper 291 may be positioned within or outside the bore 261. In various embodiments, the scraper 291 may employ various mechanisms to scrape the screen filter 225a. For example, the scraper 291 may include one or more extensions such as bristles or rigid or elastomeric flaps, for example, configured to contact the inwardly or outwardly facing surfaces 265, 267 of the annular wall 259 or body 253. In the illustrated embodiment, the scraper 291 includes a spray bar 293 having one or more fluid ports 295 configured to direct a fluid onto the annular wall 259 to clean the screen filter 225a, e.g., to dislodge solid components from the filter portion 255 or encourage solid components 231 to move along a lower portion of bore 261 by the action of the screw 285. In at least one embodiment, the spray bar 293 is positioned within the bore 261 to direct fluid onto the inwardly facing surface 265 of the annular wall 259, e.g., along the filter portion 255 or bands 275. In some embodiments, multiple spray bars 293 or fluid ports 295 may also be positioned around the body 253 or both within the bore 261 and along the outwardly facing surface 267. The fluid ports 295 may include nozzles 297 configured to directionally enhance or modulate distribution of the cleaning fluid. In certain embodiments, the fluid ports 295 may be statically positioned. Regulation of volume or pressure of cleaning fluid directed from the fluid ports 295 may be modulated using pumps, restriction or obstructive elements, valves, etc. For example, in one embodiment, an orifice plate may be disposed in the spray bar 293. The orifice plate may be positioned to modulate flow for a single or multiple fluid ports 295, for example. In at least one embodiment, the fluid ports 295 may be movable via the central control unit 32, 164, e.g., in a predetermined or programmed pattern or selectively, which may include sensors configured to sense locations in need of the cleaning action of the fluid and that which send such data to the central control unit 32, 164 for automated directing. In this or another embodiment, the fluid ports 295 may be manually directed via remote controls provided by a user remote control system incorporated with the central control unit 32, 164.

In one embodiment, the upstream filter 225 may be configured as a modular unit or pallet for augmentation of a capture unit, such as capture units 15, 115, of a new or existing application system 10 to thereby filter the solid component 231 of desired size from the effluent 223. The upstream filter 225 may therefore include various fittings or attachment points configured to couple to new or existing application systems 10.

The capture unit 215 may further include a capture tank 216. The capture tank 216 may be positioned along the downstream capture line 237 between the upstream and downstream filters 225, 227 and may include a reservoir 218 for retaining effluent 223. The capture tank 216 may include an inlet 220 to receive the upstream effluent filtrate 235 from the upstream filter 225. The upstream filter 225 may direct or the inlet 220 of the capture tank 216 may be positioned to receive the upstream effluent filtrate 235 directly from the upstream filter 225, as generally shown in FIGS. 5 & 6. For example, the inlet 220 or reservoir 218 may be positioned adjacent to and downstream of the filter portion 255. In some embodiments, additional capture tanks 216 may be included, e.g., the screen filter 225a may include a capture tank 216 position to catch upstream effluent filtrate 235 passed through the filter portion 255 which may subsequently be passed to the downstream capture line 237, which may include an additional capture tank 216. In at least one embodiment, the capture tank 216 is disposed between a first portion of the downstream capture line 237a and a second portion of the downstream capture line 237b, as depicted in FIG. 4.

The capture tank 216 may also include an outlet 222 through which effluent 223 may be passed downstream to the downstream filter 227. The outlet 220 may be coupled to the downstream capture line 237 and include a drain or valve configured to open the outlet to allow the effluent 223 to pass from the capture tank 216 into the downstream capture line 237 toward the downstream filter 227. For example, the valve may be configured for manual actuation or automated actuation based on a time, volume of upstream effluent filtrate 235 in the reservoir 218, capacity of the downstream filter 227, etc. Automated actuation may be in response to a signal provided by the central control unit 32, 164 or the valve may be mechanically configured to actuate based on a condition of the system, e.g., an upstream or downstream pressure.

Transport of the effluent 223 from the outlet 222 toward the downstream filter 227 may be promoted, for example, by gravity or a pump disposed in or operatively coupled to the downstream capture line 237. In various embodiments, the capture tank 216 may include a siphon as shown and described above with respect to FIG. 1. For example, the siphon may be fluidically coupled to the downstream capture line 237. The siphon may be configured to allow the upstream effluent filtrate 235 to collect in the capture tank 216, until it reaches a desired level, wherein the siphon thereafter empties or relieves a predetermined volume of the upstream effluent filtrate 235 from the capture tank 216 and passes the effluent 223 through the downstream capture line 237 toward the downstream filter 227. By incorporation of the siphon or other mechanism configured to avoid continuous passage or trickle of effluent 223, e.g., using valves configured to be actuated at various time intervals or upon receiving an actuation signal from the central control unit 32, 164 or sensor configured to monitor the level of effluent in the capture tank 216, the capture unit 215 may reduce or eliminate incidences of channeling with respect to the downstream filter 227. In at least one embodiment, however, the capture unit 215 does not incorporate a siphon or other mechanism configured to avoid continuous passage of effluent 223. In one such embodiment, the capture unit 215 does not include a capture tank 216, rather the downstream capture line 237 is positioned to collect the upstream effluent filtrate 235 from the screen filter 225a and pass the upstream effluent filtrate 235 directly to the downstream filter 227 for continuous processing of the effluent 223 transported to the capture unit 215. As such, the capture unit 215 may be configured for continuous capture and disposal of effluent 223.

The downstream filter 227 may include an antimicrobial separation unit 241 as described above and generally shown in FIGS. 4-6. The antimicrobial separation unit 241 may include one or more filter units 227a, 227b, such as disposable carbon filters 108, as described above with respect to FIG. 1, for selective removal of the antimicrobial component 228 from the effluent 223, wherein the antimicrobial is preferably a quaternary ammonium compound, an alkylpyridinium chloride, or cetylpyridinium chloride. Intermediate filter line 239 extends between the filter units 227a, 227b for transporting intermediate effluent filtrate 249 from filter unit 227a to filter unit 227b. As described above, the filter units 227a, 227b may be configured to exploit one or more characteristics of the effluent 223 or its components to achieve the desired separation of the antimicrobial component 245 from the effluent 223 using any suitable filter strategy and design. In the illustrated embodiment, the filter units 227a, 227b of the separation unit 241 of the downstream filter 227 include at least two filter units that are aligned in series. Each filter unit 227a, 227b includes a container 242 for housing a filter material 243, such as activated carbon, through which the upstream effluent filtrate 235 may be passed for separation of the antimicrobial microbial component 245, e.g., via reaction or adsorption onto the filter material 243. While two filters units 227a, 227b are shown, additional filters may be used. For example, in one embodiment, the downstream filter 227 includes a separation unit 241 having between two and four filter units 227a, 227b aligned in series, wherein each filter unit 227a, 227b includes a container for retaining a supply of filter material 243 including activated carbon.

The downstream filter 227 may include an outlet configured to be coupled to a disposal line 247 to allow downstream effluent filtrate 249 to exit the separation unit 241. In various embodiments, the separation unit 241 is configured to separate a suitable quantity of antimicrobial component 245 from the upstream effluent filtrate 235 such that the resultant downstream effluent filtrate 249 is characterized as having suitably low levels of contaminants or antimicrobial component 245 such that the downstream effluent filtrate 249 is suitable for disposal as plant wastewater discharge in compliance with current effluent guidelines.

Figure 7:
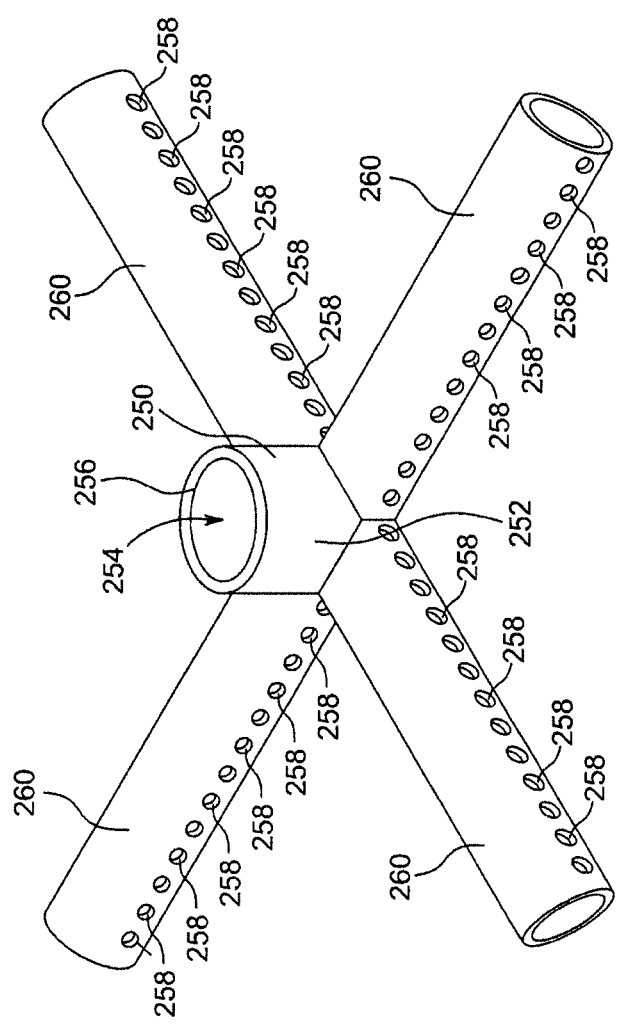
FIG. 7 is a perspective view of a header according to various embodiments described herein.

In various embodiments, and in further reference to FIG. 7, the antimicrobial separation units 106, 160, 241 may include a header 250. The header 250 is preferably configured to distribute effluent 223, such as upstream or an intermediate downstream effluent filtrate 235, 249, evenly with respect to the filter material 243, however, in at least one embodiment, the header 250 may be configured to selectively distribute the effluent 223 to one or more regions of the filter material 243 within the container 242. The header 250 includes a body 252 defining an internal fluid path 254 that extends between an upstream inlet 256 and a plurality of downstream fluid ports 258. The body 252 may include one or more arms 260 into which fluid ports 258 may be formed to distribute the effluent 223. The arms 260 may include various arrangements of fluid ports 258 patterned thereon. In the illustrated embodiment, the header 250 includes four arms 260, and may be constructed from piping, for example, and arranged in a crossing or "X" configuration. In other embodiments, however, the header 250 may include other configurations with fewer or additional arms, which may further include secondary arms.

The fluid ports 258 are aligned along two sides of each arm 260. However, in some embodiments, the fluid ports 258 may be aligned along a single side, circumferentially, or along three or more sides of the arms 260 or as otherwise desired to distribute the effluent 223 of effluent filtrate 235, 249 and reduce channeling. For example, as introduced above, even distribution may be desirable to prevent channeling or to increase surface contact between the effluent 223 and the filter material 243. The number and dimensions of the fluid ports 258 may vary to optimize distribution, for example, in consideration of the characteristics of the fluid, filter material 243, or flow conditions. As such, the fluid ports 258 may be dimensioned to restrict, direct, spray, or focus the fluid exiting the fluid path 254. As shown, each of the arms includes twenty-six fluid ports 258. In at least one embodiment, each of two or more arms 260 includes twenty fluid ports. As shown, the header 250 also includes fluid ports 258 having cross-sections between 0.125 to 0.250 inches. However, as described above, additional dimensions and features could also be used depending on the environment in which the system 10 operates. For example, in one embodiment, the header 250 is configured to be movable to increase dispersion of the effluent 223. For instance, the header 250 may be adapted to rotate or selectively move according to a pre-determined pattern. The rate or degree of movement for example may be related to the amount of effluent 223 passing through the header.

Figure 8:
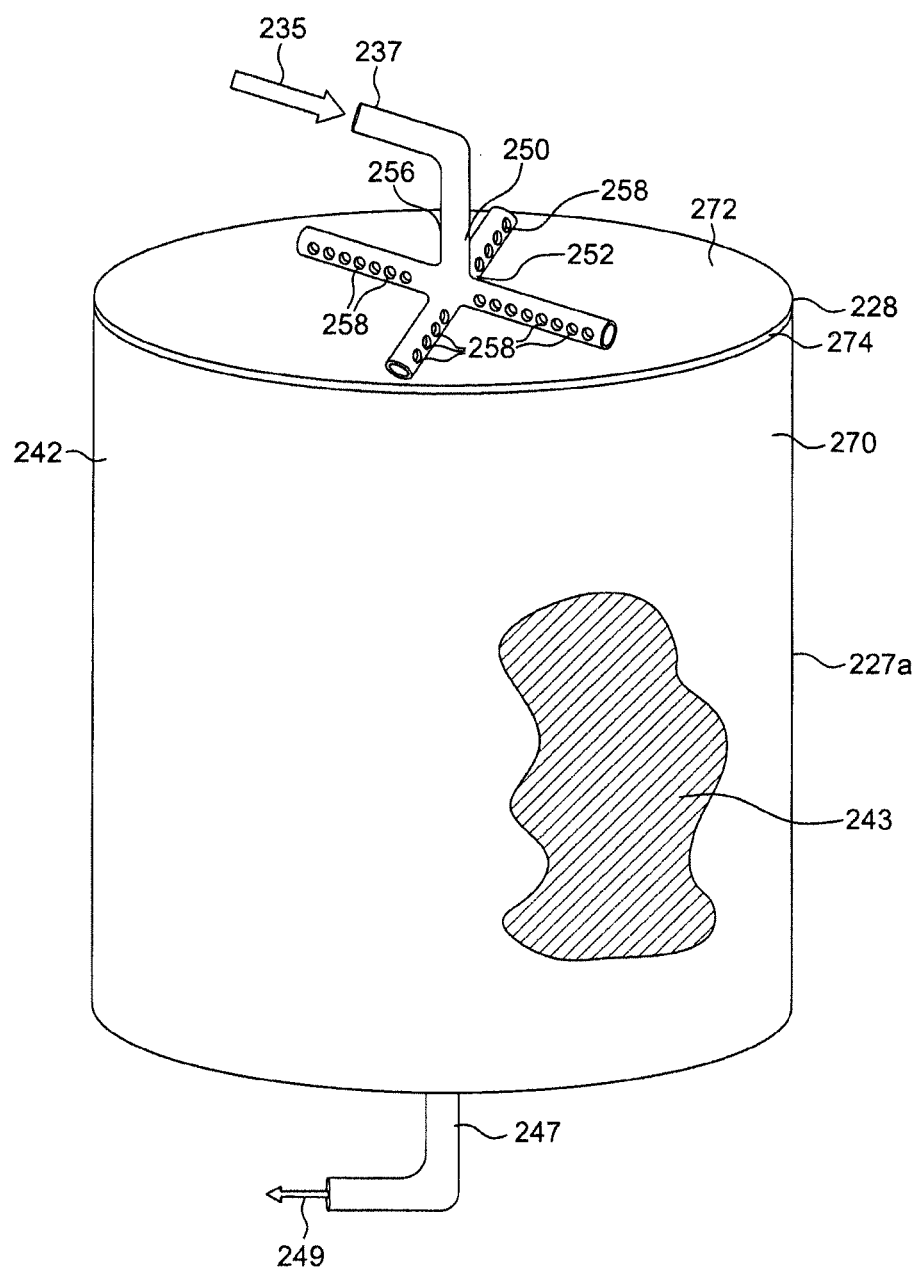
FIG. 8 is a perspective view of a filter unit according to various embodiments described herein.

FIG. 8 illustrates the header 250 positioned in the filter unit 227a shown in FIGS. 4-6 according to various embodiments. The header 250 may be employed in a carbon filtration system including at least two filter units 227a, 227b, 108, as described above. It is to be appreciated, however, that filter units 227a, 227b, 108 do not necessarily include a header 250 or the illustrated header 250. Indeed, in at least one embodiment, filter units 227a, 227b, 108 include different headers. Similarly, the filter units 227a, 227b, 108 may be configured to retain the same or different filter material 243. In one embodiment, one or both of the filter units 227a, 227b shown in FIG. 5 may include the header 250. As described above, the filter units 227a, 227b, 108 may include containers 242 configured to retain filter material 243. The container may include an inner surface 272 or liner 274 configured to be positioned adjacent to the filter material 243. The header 250 may be suitably positioned at an upstream portion of the container 242 to receive upstream effluent filtrate 235 from the downstream capture line 237 or an intermediate downstream effluent filtrate 249 from the intermediate filter line 239, as the case may be, and therein distribute the fluid onto the filter material 243. In the illustrated embodiment, the inlet 256 of the header 250 is configured to couple to the downstream capture line 237 to receive the upstream effluent filtrate 235 within the fluid path 254. The header 250 is positioned over the filter material 243 and is configured to distribute the upstream effluent filtrate 249 onto the filter material 243 positioned within the container 242. In operation, the header 250 may be attached to or be positioned within the container 242, which may include a filter drum for example. Distribution provided by the header 250 may reduce or inhibit channeling through the container 242. For example, the header 250 may distribute or sprinkle received effluent 223 or effluent filtrate 235, 249 over a top surface of the filter material 243 to thereby achieve increased distribution and little to no channeling through the filter material 243.

In various embodiments, the antimicrobial separation units 106, 160, 241 may include a filter unit 227a, 227b, 108 in which the container 242 includes a plastic or plastic lined drum configured to contain filter material 243 comprising activated carbon. As described above, the filter unit 227a, 227b, 108 may be disposable such that the activated carbon may be properly disposed of when spent. In contrast to conventional filter units 227a, 227b, 108 and containers 242, which are typically formed of metals susceptible to corrosion during their operational lifetime in a capture unit 15, 115, 215, the plastic drum may be configured to avoid such corrosion that may otherwise lead to the occurrence of leaks.

Figure 9:
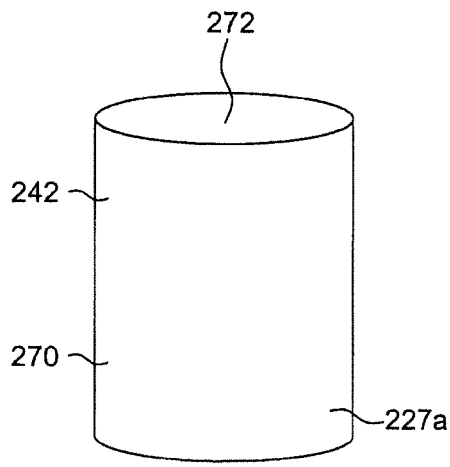
FIG. 9 is a perspective view of a filter unit container according to various embodiments described herein.
Figure 10:
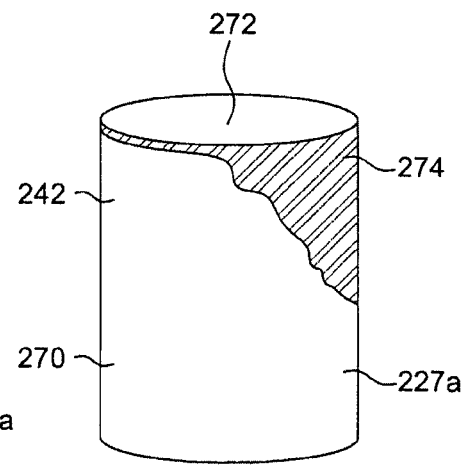
FIG. 10 is a perspective view of a filter unit container according to various embodiments described herein.
Figure 11:
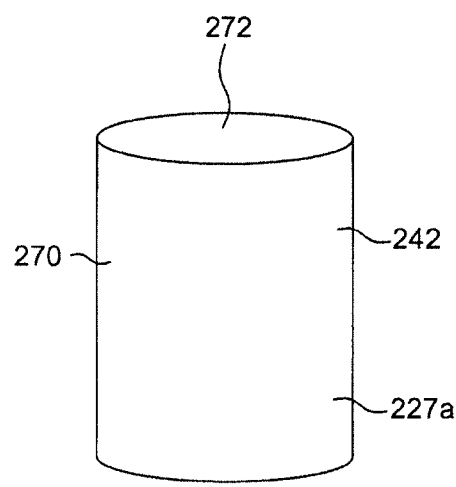
FIG. 11 is a perspective view of a filter unit container according to various embodiments described herein.

FIGS. 9-11 illustrate embodiments of containers 242 suitable for use in the filter units 227a, 227b, 108 described above for improved integrity of the system 10 or an antimicrobial carbon filtration system. As introduced above, conventional metallic containers, commonly referred to as drums, used in filter units 227a, 227b, 108 have been found to be susceptible to premature loss of integrity during their operational lifetimes. This loss of integrity is believed to be a result of corrosion produced in the corrosive environment of the antimicrobial separation unit 241. In the embodiments illustrated in FIGS. 9-11, the containers 242 include inner surfaces 272 or liners 274 composed of a non-corrosive material.

FIG. 9 illustrates a container 242 having an outer surface 270 and an inner surface 272. The outer surface 270 may include a conventional metallic material. In other embodiments, however, the outer surface 272 may include a hard plastic, a ceramic, a rigid material, or other suitable material. The inner surface 272 may include a coating formed along a container shell or outer surface 270 material. The coating may include a plastic, polymer, resin, enamel, ceramic, epoxy, anti-corrosive, or a combination or blend thereof.

FIG. 10 illustrates an alternate embodiment of the container 242 wherein the inner surface 272 is formed as a liner 274. The liner 274 may be configured to be selectively inserted and removed from within the outer surface 270. In one embodiment, the liner 274 and the inner surface 272 may be further formed of a resilient elastomeric material that may be compressably retained within the outer surface 270. Other manners of retaining the inner surface 272 within the outer surface 270 may include fittings adhesives, flanges, brackets, or fittings employing latches, threads, clamps, bolts, hooks and grooves, or screws, for example.

FIG. 11 illustrates another embodiment of the container 242 wherein both the inner and outer surfaces 270, 272 may be formed of the materials described above with respect to FIGS. 9 and 10. For example, the container 242 may include a plastic drum configured to retain filter material 243, such as activated carbon.

It is to be appreciated that the choice of inner surface material in the embodiments illustrated in FIGS. 9-11 should be one that is preferably resistant to integrity damaging corrosion during its operational lifetime within its operational environment. For example, the inner surface material should be resistant to corrosion within the environment produced by the effluent 223 or when the effluent 223 mixes or reacts with filter material comprising activated carbon.

Other modifications, changes and substitutions are intended in the foregoing, and in some instances, some features will be employed without a corresponding use of other features. For example, the different features of the alternate embodiments may be merged or combined in any number of different combinations. Also, the antimicrobial application unit 12 may take any number of forms, shapes, and sizes and need not be one of the spray cabinet embodiments disclosed in U.S. Pat. No. 6,742,720. Similarly, any number of different compositions may be used in any number of different concentrations, and the compositions may or may not include one or more antimicrobials. Further still, additional pumps, filters, and similar components may be incorporated into the system 10. Also, any number of different methods may be used to monitor the composition of the composition in the recycle tank 24. Similarly, the composition may be monitored constantly or at desired intervals. Further still, the drip tray 22 may not be used and may be any number of different lengths. Of course, quantitative information is included by way of example only and is not intended as a limitation as to the scope of the invention. Accordingly, it is appropriate that the invention be construed broadly and in a manner consistent with the scope of the invention disclosed.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification. In this manner, Applicant reserves the right to amend the claims during prosecution to add features as variously described in this specification, and such amendments comply with the requirements of 35 U.S.C. §§ 112(a) and 132(a).

What is claimed is:

1. A method for capturing an antimicrobial component of an antimicrobial solution, comprising:

filtering a solid component from an antimicrobial solution with a first filter coupled to a capture line for carrying the antimicrobial solution to the first filter;

conveying the antimicrobial solution from the first filter to a second filter;

filtering an antimicrobial component from the antimicrobial solution with the second filter;

wherein the first filter comprises a screen filter having a rotatable body, wherein the body comprises an annular wall having an inwardly facing surface defining a bore to receive the antimicrobial solution from the capture line, and wherein the annular wall comprises:

a filter portion defining a plurality of holes along the inwardly facing surface that extend through the annular wall to filter the solid component of the antimicrobial solution when the antimicrobial solution is received thereon from the capture line, and a band portion having a continuous surface that extends about the bore along the inwardly facing surface to receive the antimicrobial solution from the capture line onto the continuous surface before the antimicrobial solution is received along the filter portion, and wherein the capture line comprises an outlet positioned to direct the antimicrobial solution onto the continuous surface of the band at an angle between less than parallel and perpendicular to the inwardly facing surface.

2. The method of claim 1, wherein the screen filter further comprises a thread protruding from the inwardly facing surface of the annular wall into the bore, and wherein the thread helically extends along the inwardly facing surface between a first end and a second end of the body.

3. The method of claim 2, wherein the thread extends along the filter portion and the continuous surface.

4. The method of claim 1, further comprising removing the filtered solid component from the annular wall with a cleaner associated with the screen filter.

5. The method of claim 4, wherein the cleaner comprises a spray bar including one or more fluid ports positioned to direct fluid toward an outwardly facing surface of the annular wall.

6. The method of claim 5, wherein the one or more fluid ports are positioned outside the bore.

7. The method of claim 1, wherein the second filter comprises at least two filter units connected by intermediate filter lines, wherein each of the at least two filter units comprises a container retaining a filter material comprising activated carbon, wherein the at least two filter units are aligned in series and are configured to filter the antimicrobial component from the antimicrobial solution, and wherein the antimicrobial component comprises a quaternary ammonium compound.

8. The method of claim 7, wherein the antimicrobial component is selected from the group consisting of alkylpyridinium chloride and cetylpyridinium chloride.

9. The method of claim 7, wherein at least one of the at least two filter units includes a header comprising a body having an upstream inlet and a plurality of downstream fluid ports positioned along a plurality of arms.

10. The method of claim 9, wherein the body comprises at least four arms arranged in an "X" configuration.

11. The method of claim 10, wherein the body includes at least two arms, each defining at least twenty fluid ports.

12. The method of claim 11, wherein the at least twenty fluid ports are positioned on at least two sides of each of the at least two arms.

13. The method of claim 11, wherein the at least twenty fluid ports define cross-sections between 0.125 to 0.250 inches.

14. The method of claim 9, wherein the at least twenty fluid ports are dimensioned to restrict, direct, spray, or focus a fluid exiting from the at least twenty fluid ports.

15. The method of claim 9, wherein the header is movable or rotatable to increase dispersion of a fluid exiting from the at least twenty fluid ports.

16. The method of claim 7, wherein at least one of the containers comprises an inner surface formed of a plastic.

17. The method of claim 1, wherein the solid component is filtered from the antimicrobial solution by the first filter based on a property or characteristic of the solid component selected from the group consisting of size, charge, viscosity, consistency, molecular structure, molecular interactions, residues, forces, bonding, and diffusion.

18. The method of claim 1, wherein the solid component is selected from the group consisting of large particles, solids, solids associated with liquids, viscous liquids, fat, gelatinous material and debris.

19. The method of claim 1, wherein the antimicrobial solution is conveyed by gravity from the first filter to the second filter.

20. The method of claim 1, wherein the antimicrobial solution is pumped from the first filter to the second filter.

* * * * *